United States Patent [19]
Kugler et al.

[11] Patent Number: 5,785,685
[45] Date of Patent: Jul. 28, 1998

[54] BALLOON CATHETER WITH IMPROVED PRESSURE SOURCE

[75] Inventors: Chad J. Kugler, Spring Lake Park; Daniel M. LaFontaine, Plymouth, both of Minn.

[73] Assignee: Scimed Life Systems, Inc., Maple Grove, Minn.

[21] Appl. No.: 812,390

[22] Filed: Mar. 5, 1997

Related U.S. Application Data

[63] Continuation-in-part of Ser. No. 586,514, Jan. 16, 1996, Pat. No. 5,695,468, which is a continuation-in-part of Ser. No. 308,025, Sep. 16, 1994, Pat. No. 5,545,133.

[51] Int. Cl.$^6$ .................................................. A61M 29/00
[52] U.S. Cl. ........................... 604/96; 604/99; 606/192
[58] Field of Search ............................ 604/96, 97, 99, 604/100, 101, 186; 606/192–195

[56] References Cited

U.S. PATENT DOCUMENTS 5,545,133  8/1996  Burns et al. .......................... 604/96
5,695,468  12/1997  LaFontaine et al. ................. 604/96

*Primary Examiner*—John D. Yasko
*Attorney, Agent, or Firm*—Robert E. Atkinson

[57] ABSTRACT

A balloon catheter is disclosed which includes a contrast displacement rod at least partially and slidably disposed in an elongate tubular member with a balloon connected to the distal end of the tubular member. The rod may include a stop mechanism to inhibit removal of the rod from the tubular member. A seal connected to the proximal end of the tubular member creates a liquid tight seal between the inside of the tubular member and the displacement rod. Accordingly, longitudinal actuation of the displacement rod causes the balloon to expand and/or contract. The balloon catheter may be a fixed wire, an over-the-wire or a single-operator exchange type balloon catheter. In addition, a pressure gauge may be connected to the proximal end of the tubular member. A one-way valve is also disclosed which allows the balloon catheter to be prepped via the guide wire lumen. Accordingly, the present invention negates the need for both an inflation device and an inflation lumen which results in a significant improvement in catheter performance and cost savings.

16 Claims, 27 Drawing Sheets

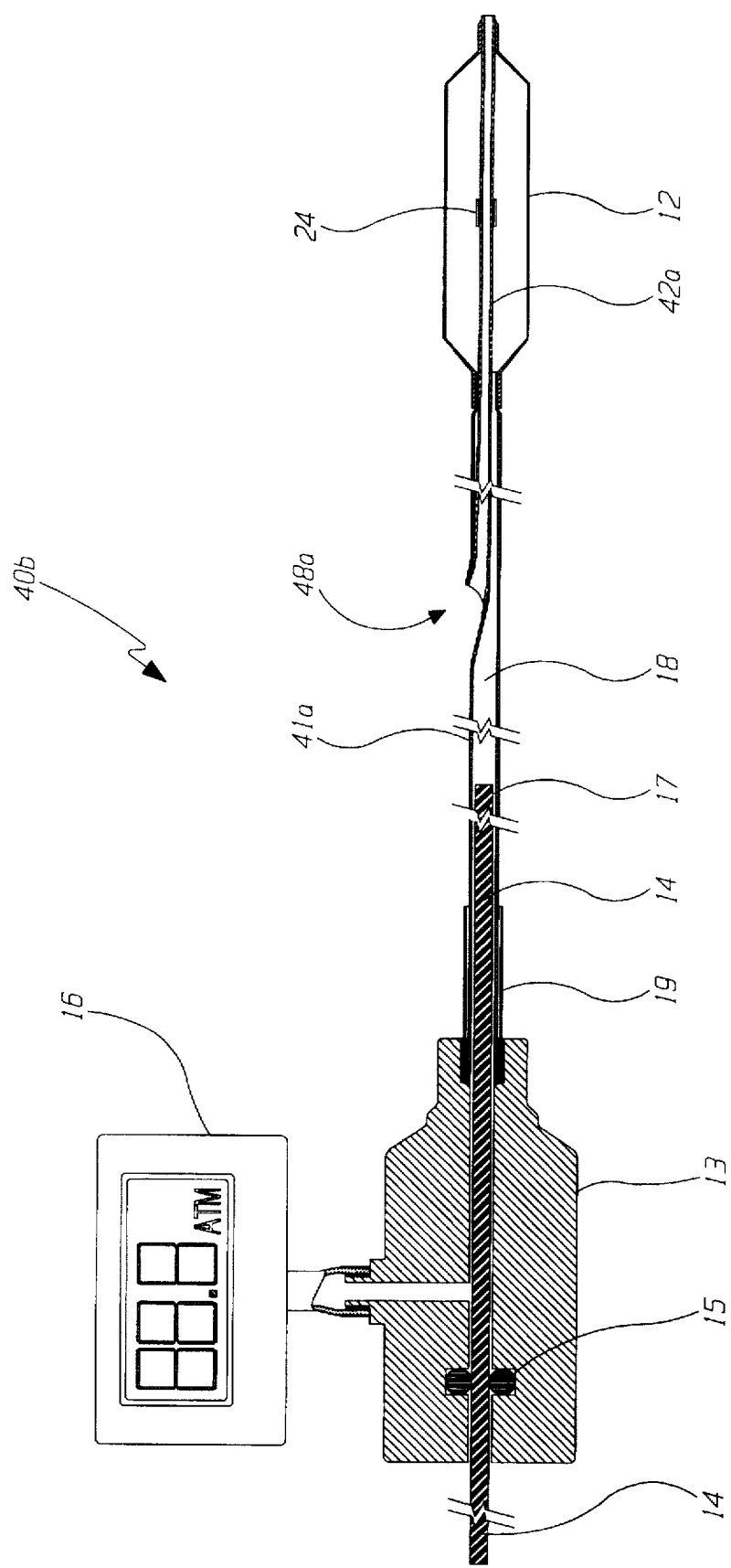

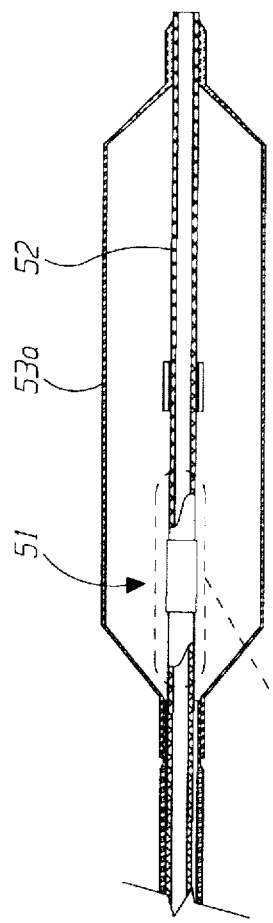
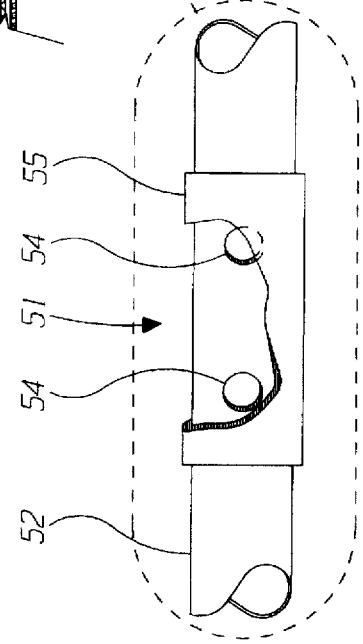
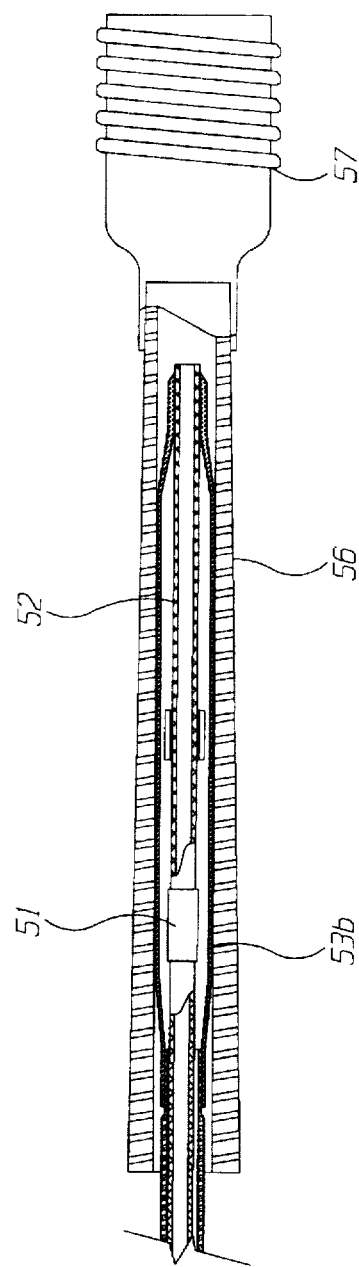
FIG. 5a
FIG. 5b
FIG. 5c

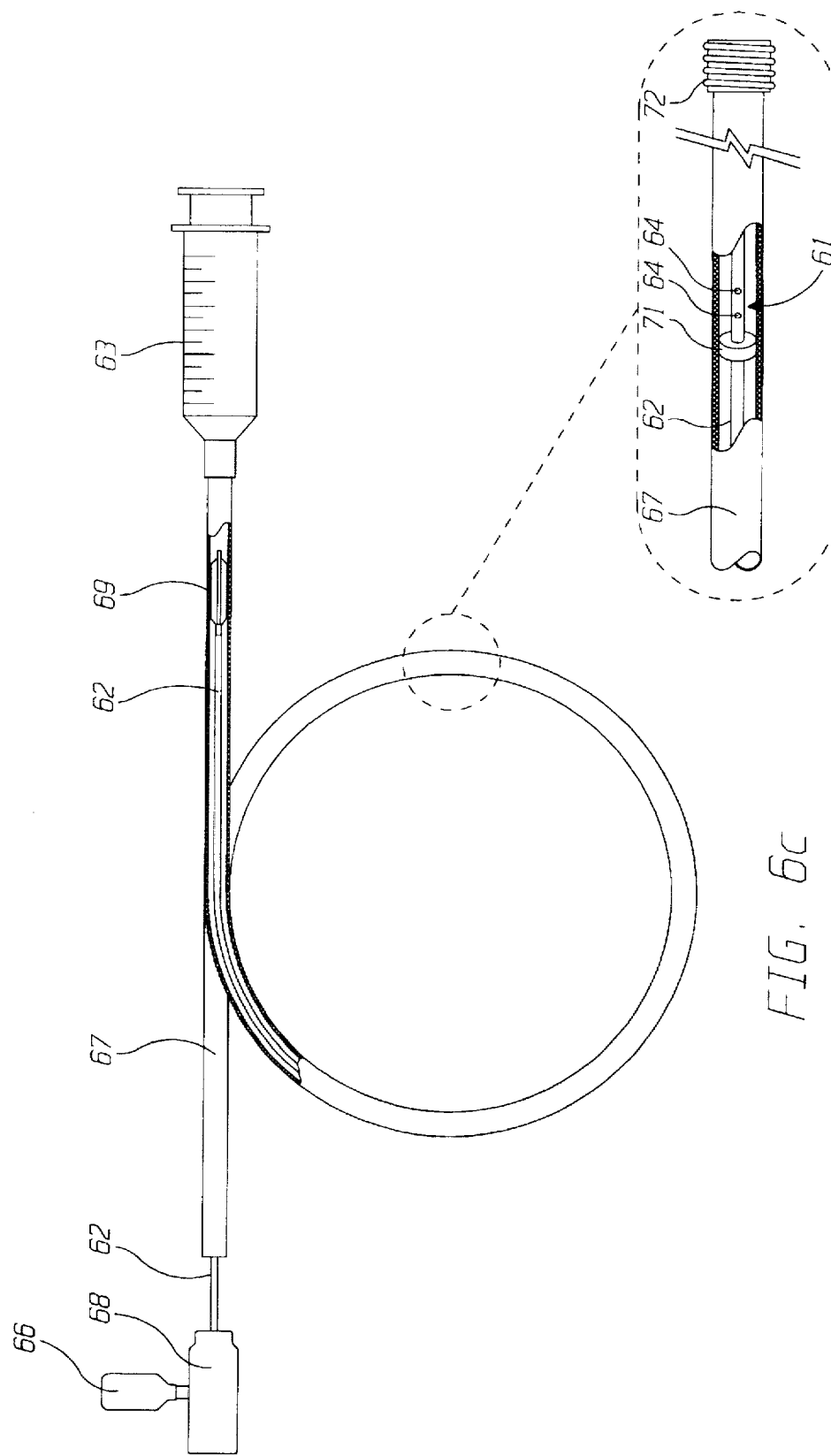

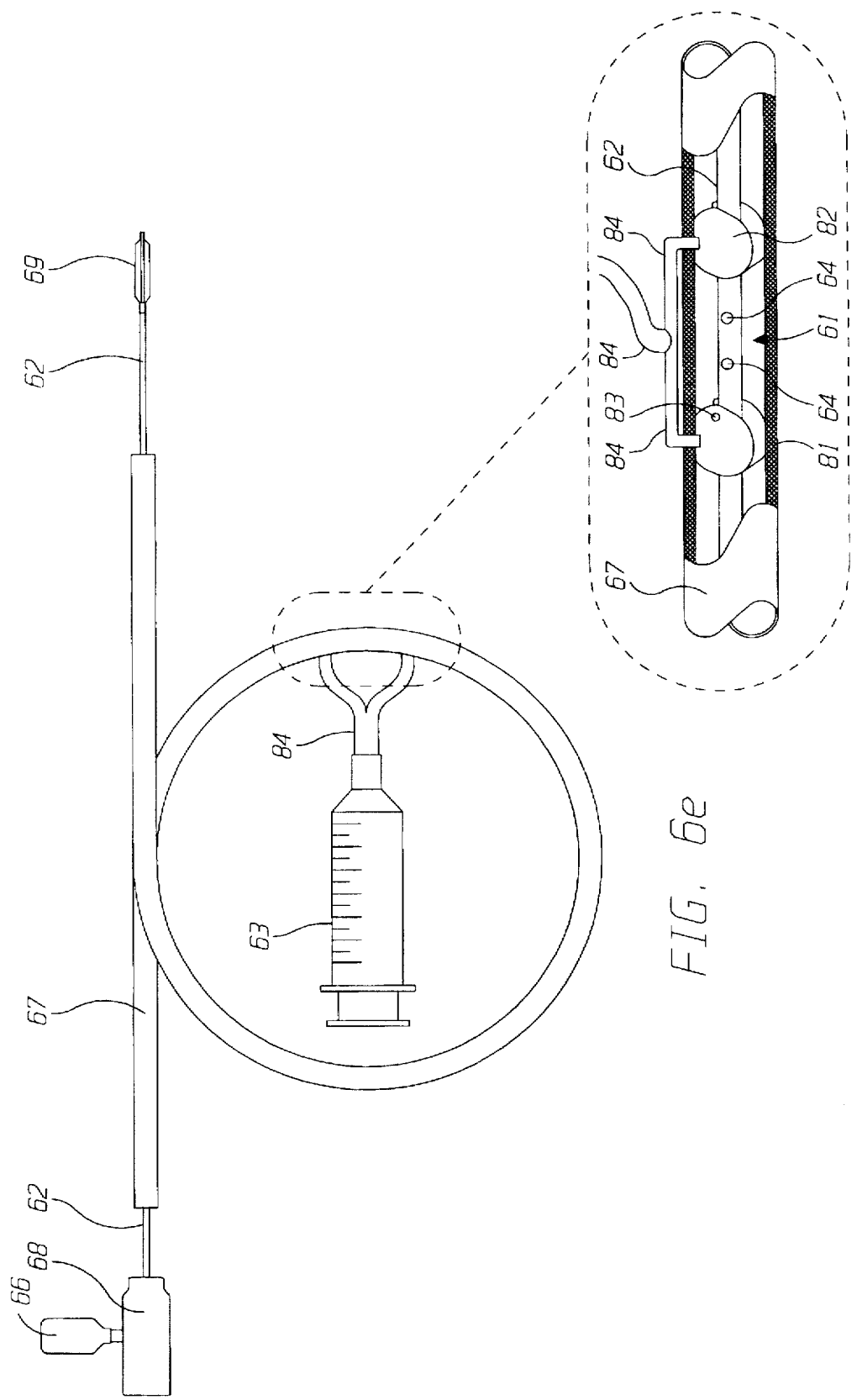

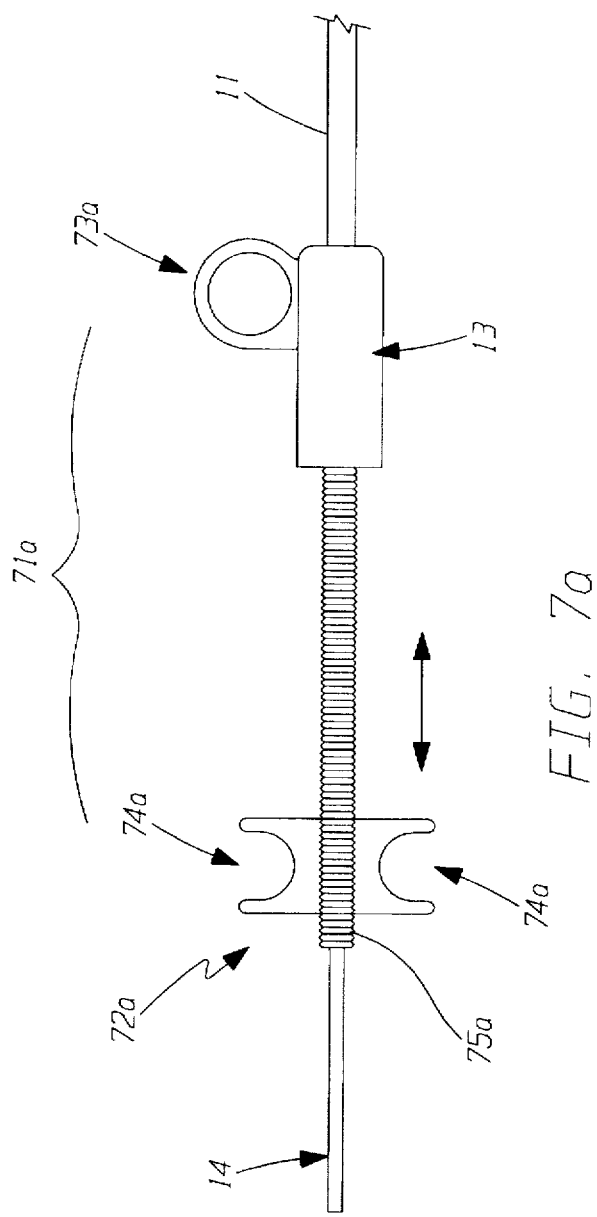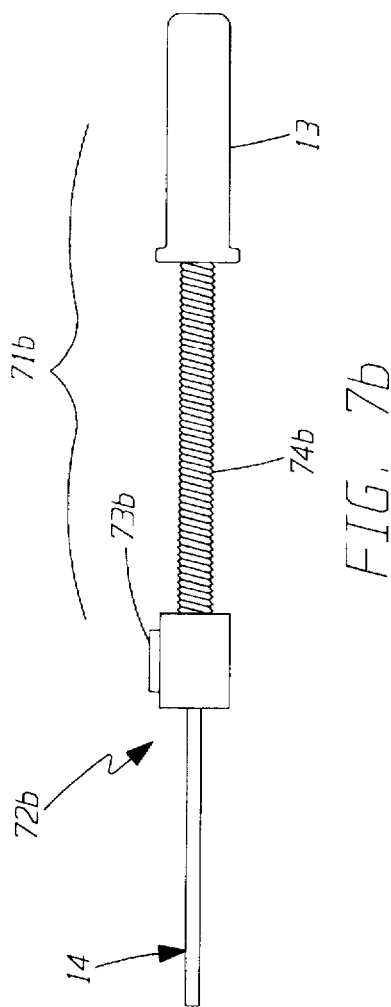
FIG. 7a
FIG. 7b

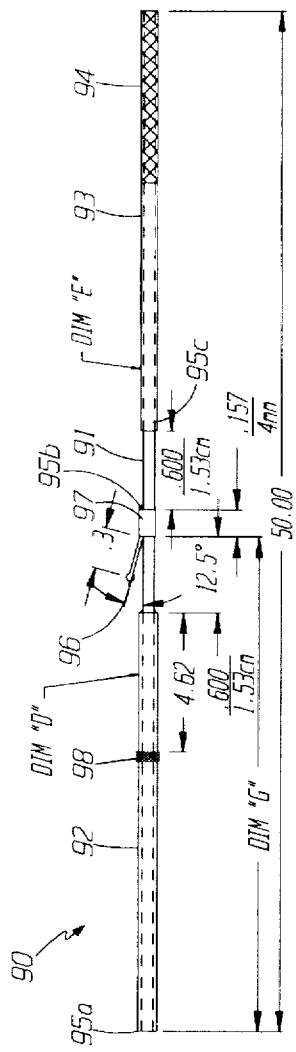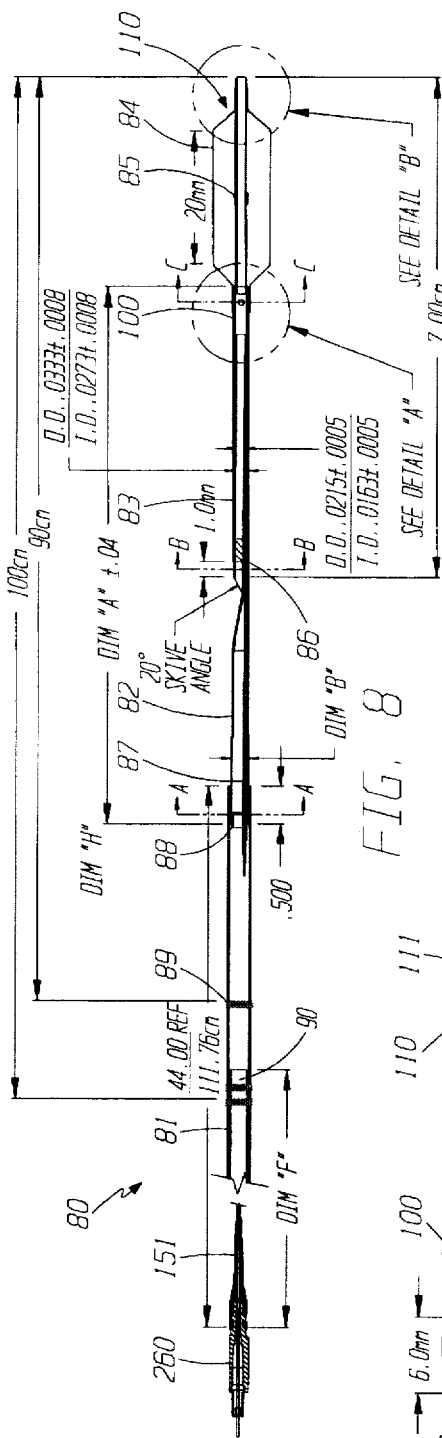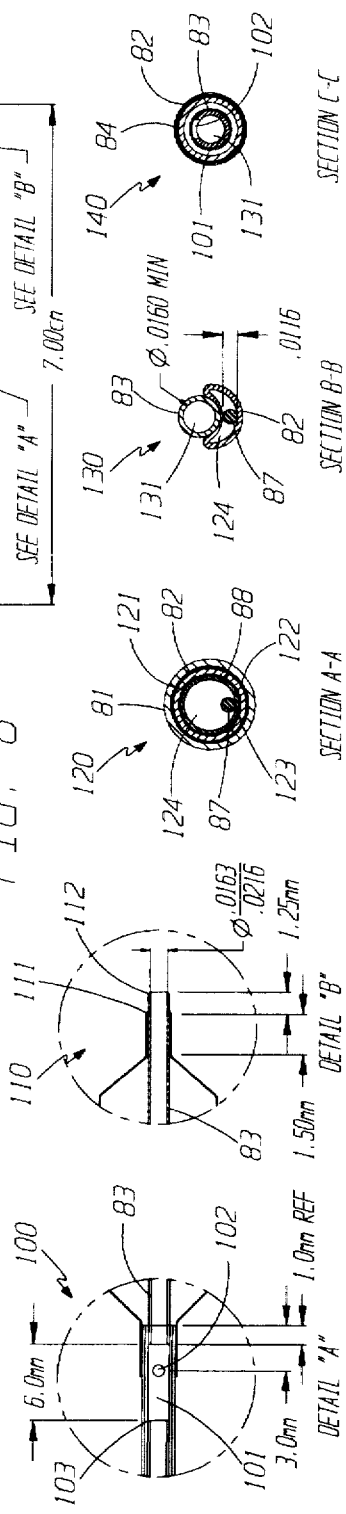

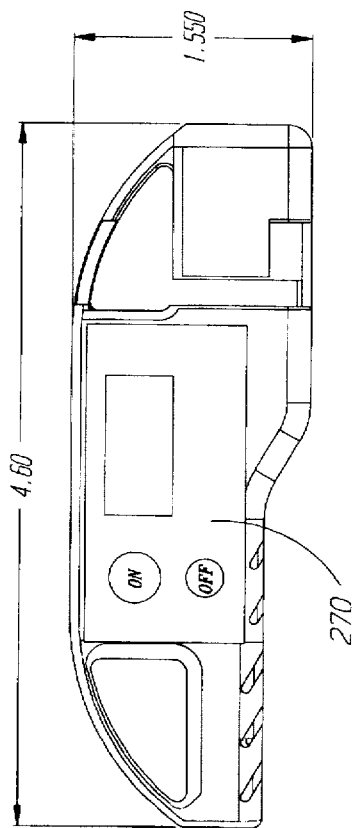
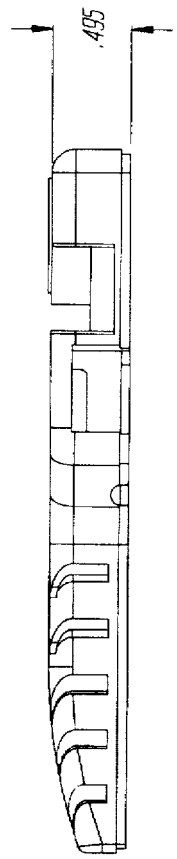
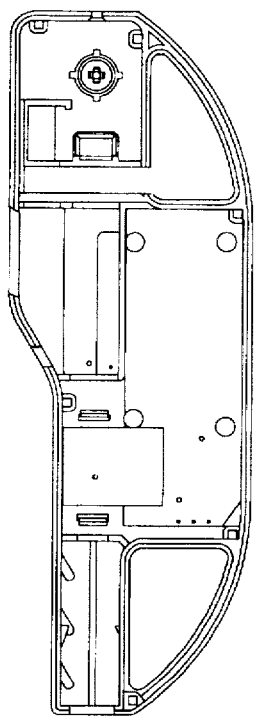
FIG. 16a
FIG. 16b
FIG. 16c

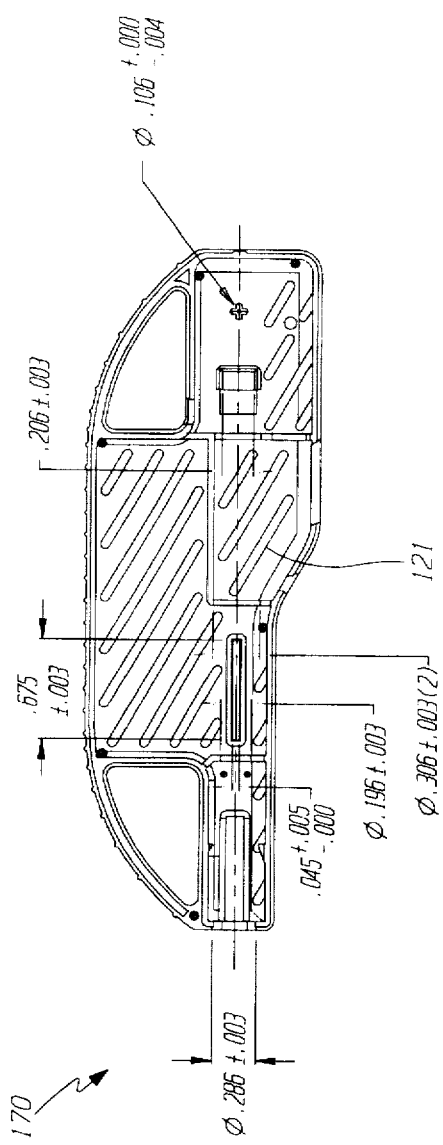
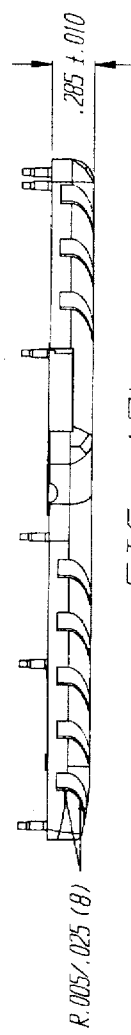
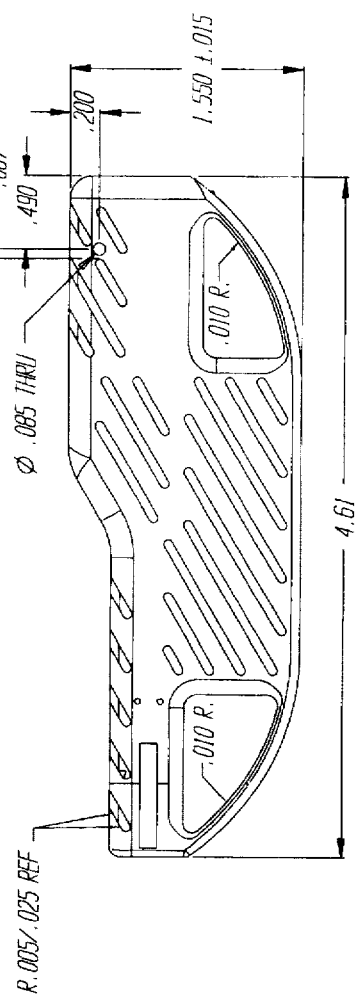
FIG. 17a
FIG. 17b
FIG. 17c

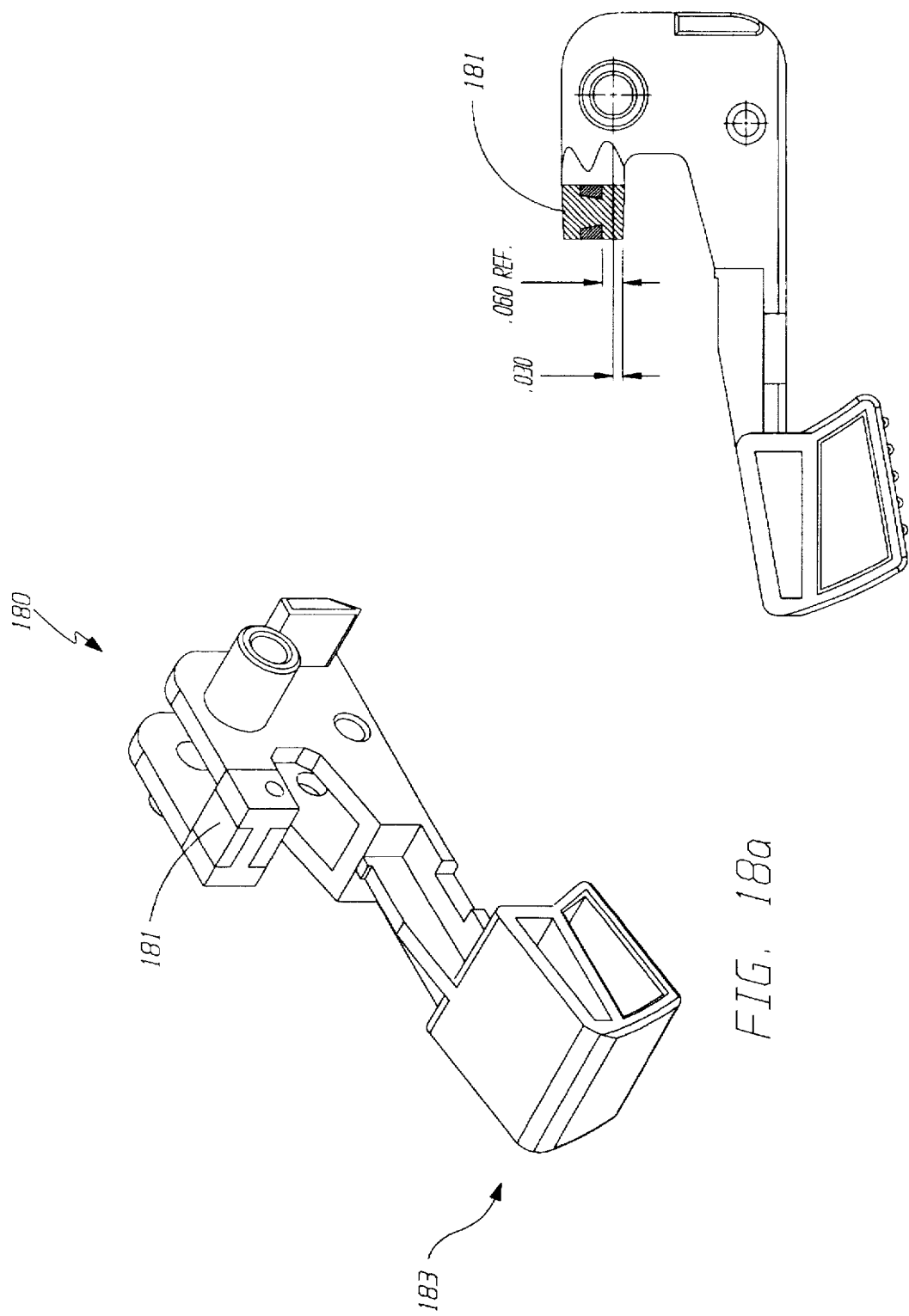

FIG. 18e
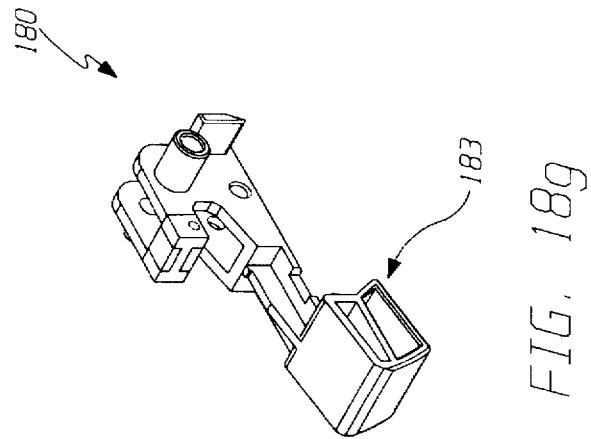
FIG. 18g
FIG. 18d
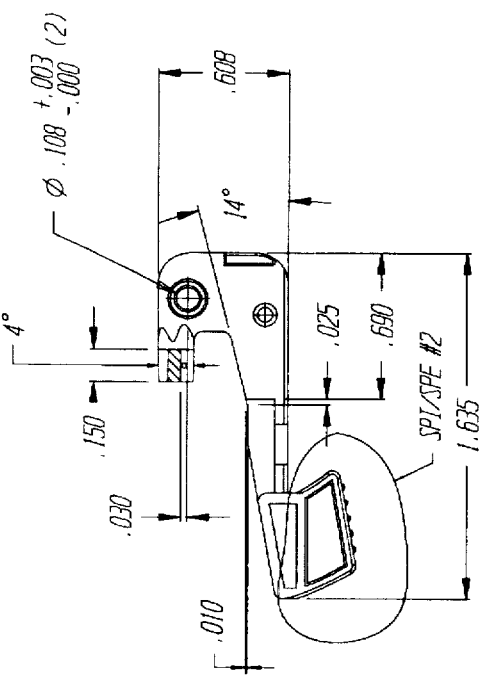
FIG. 18c
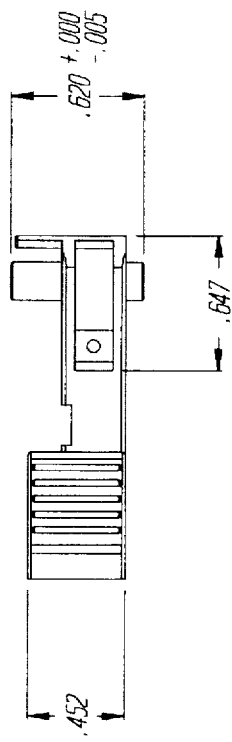
FIG. 18f

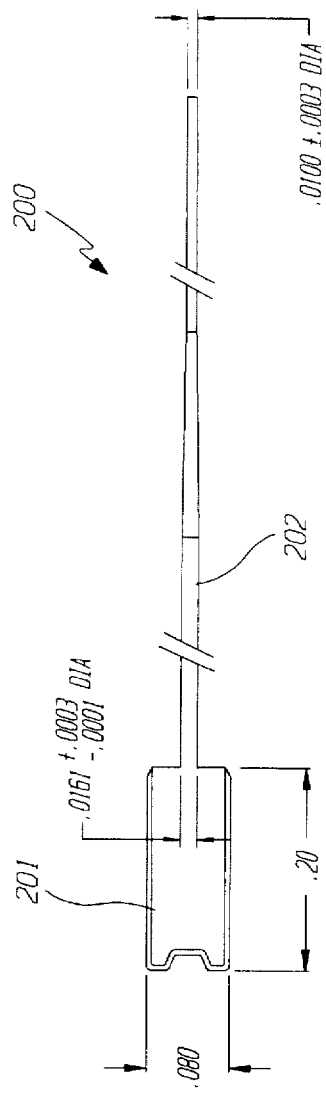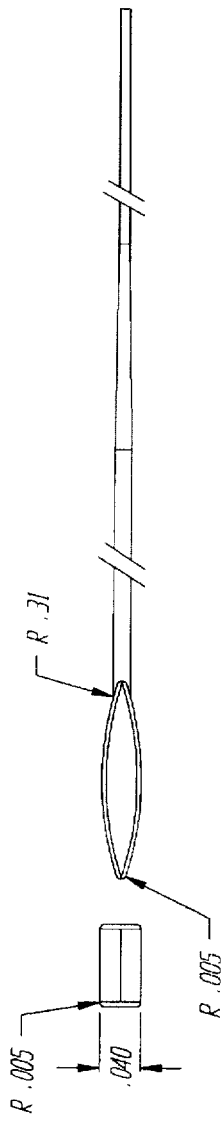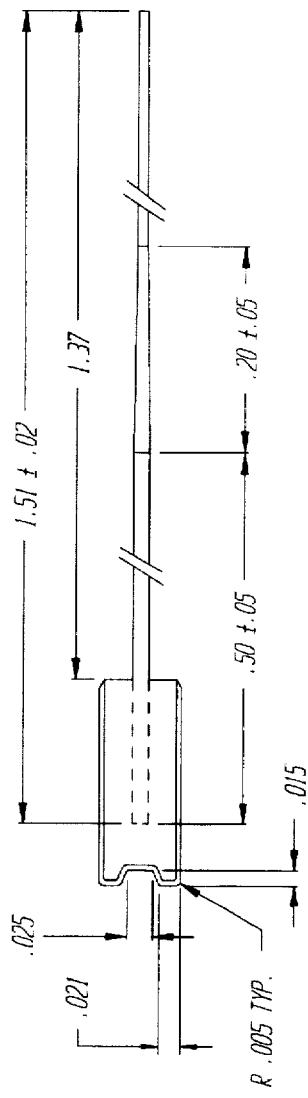

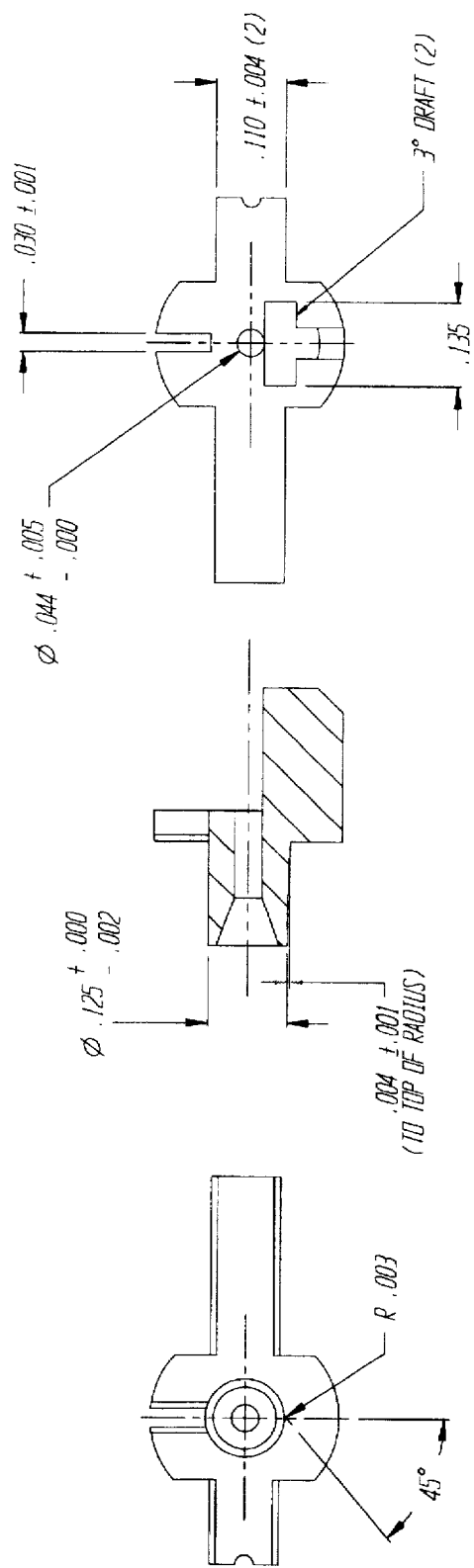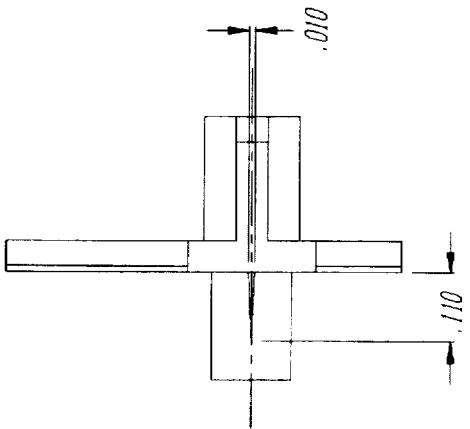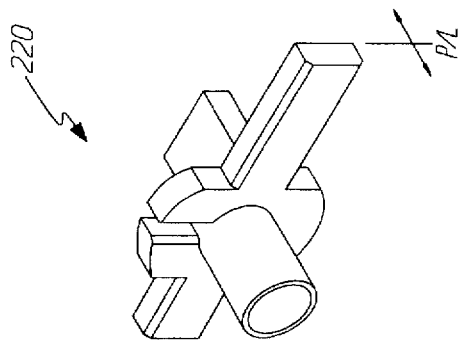
FIG. 22a
FIG. 22b
FIG. 22c
FIG. 22d
FIG. 22e

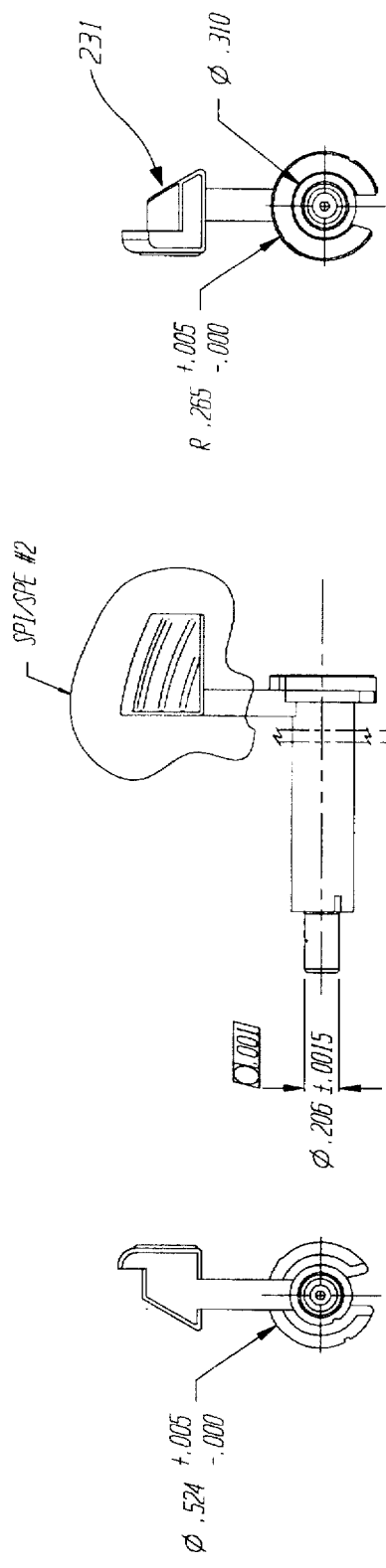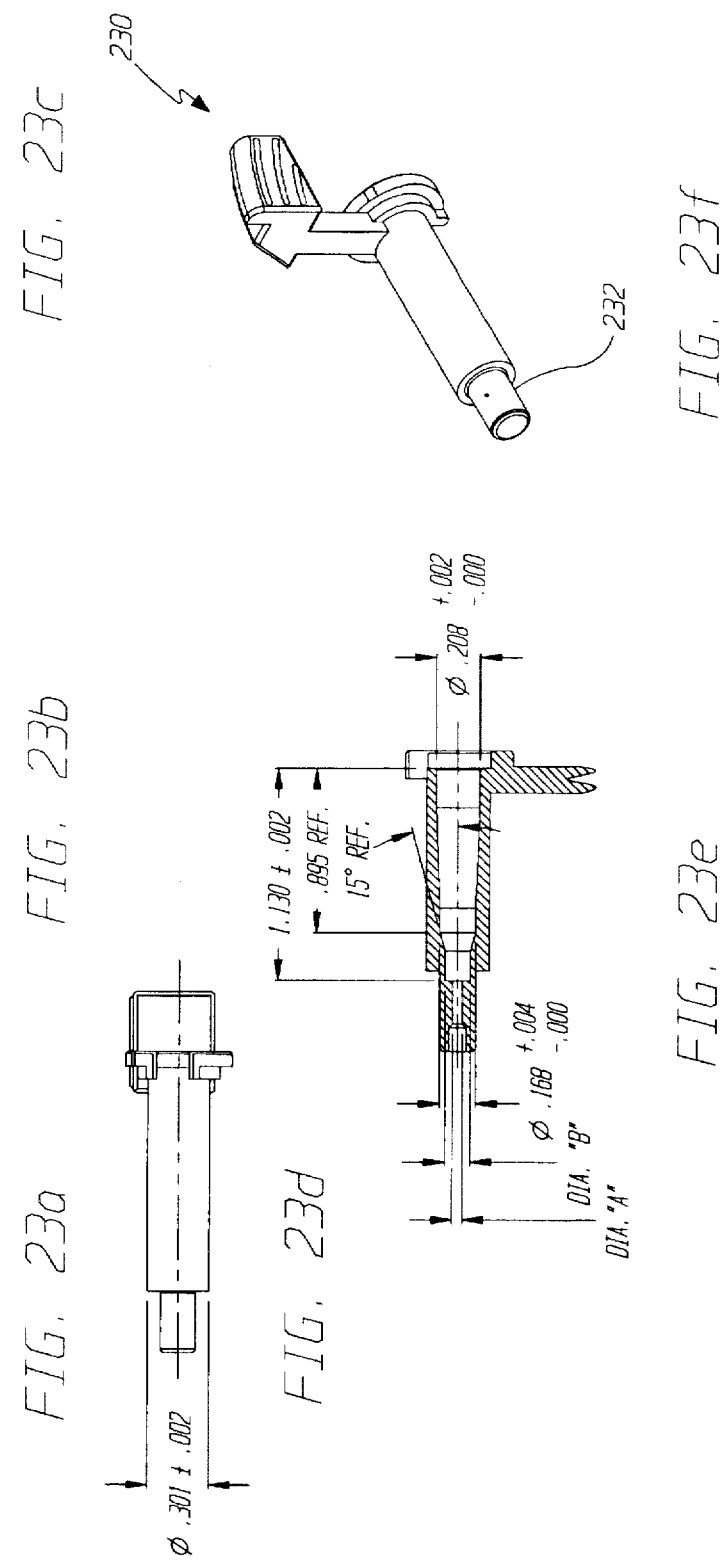
FIG. 23a
FIG. 23b
FIG. 23c
FIG. 23d
FIG. 23e
FIG. 23f

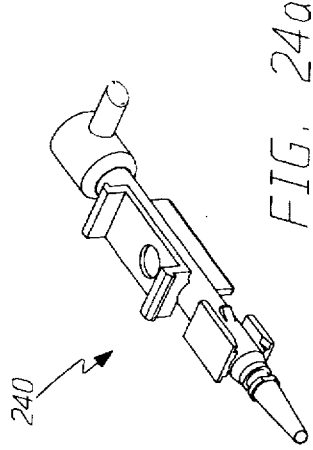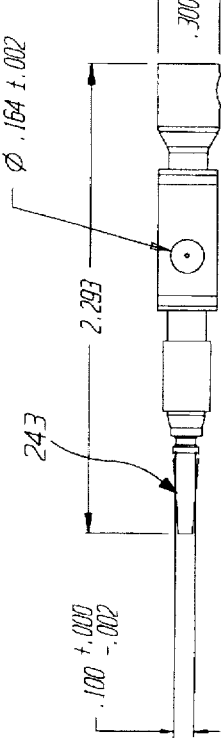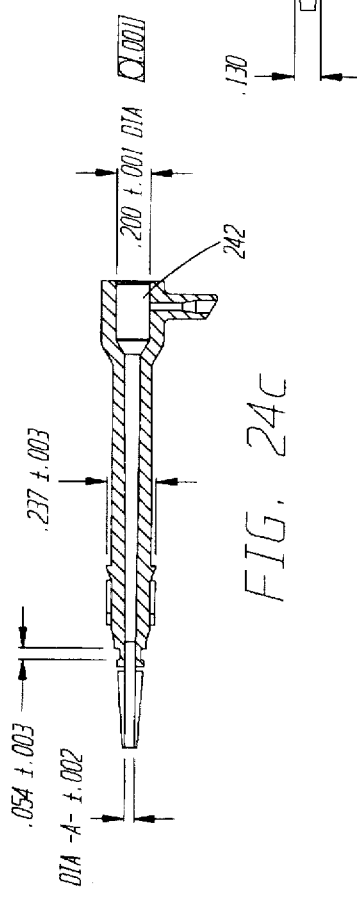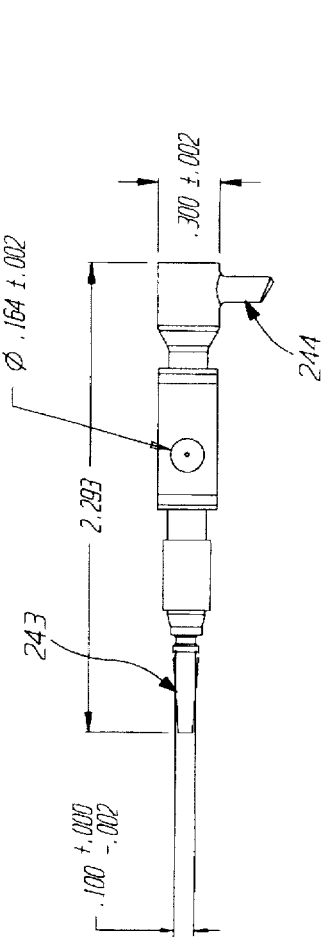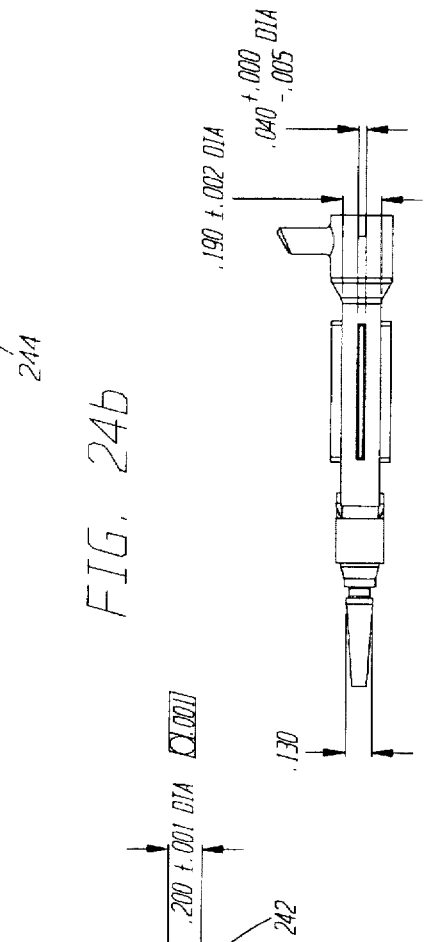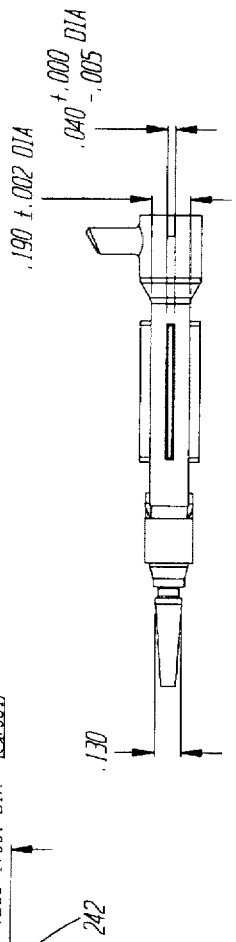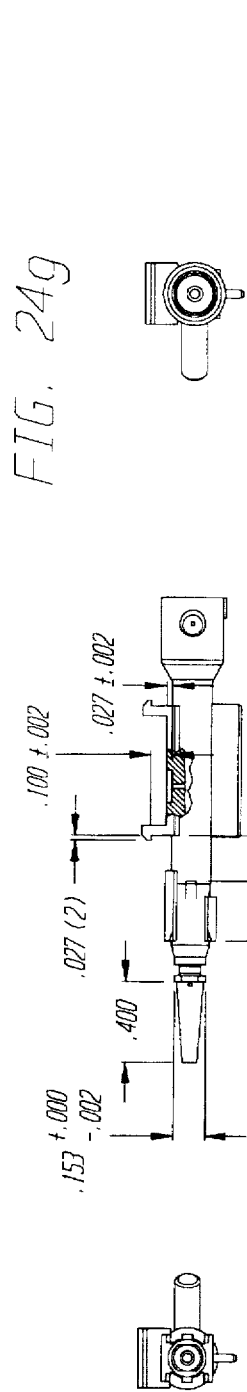

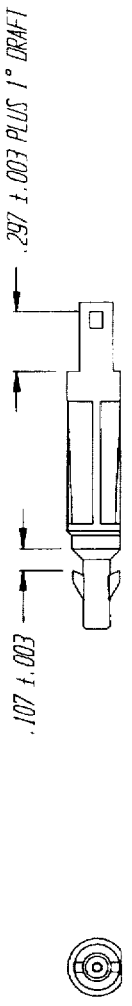
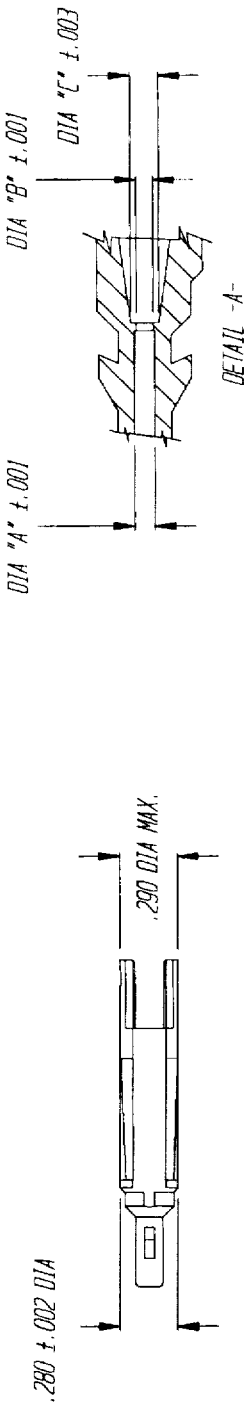
FIG. 26a
FIG. 26b
FIG. 26c
FIG. 26d
FIG. 26e
FIG. 26f
FIG. 26g

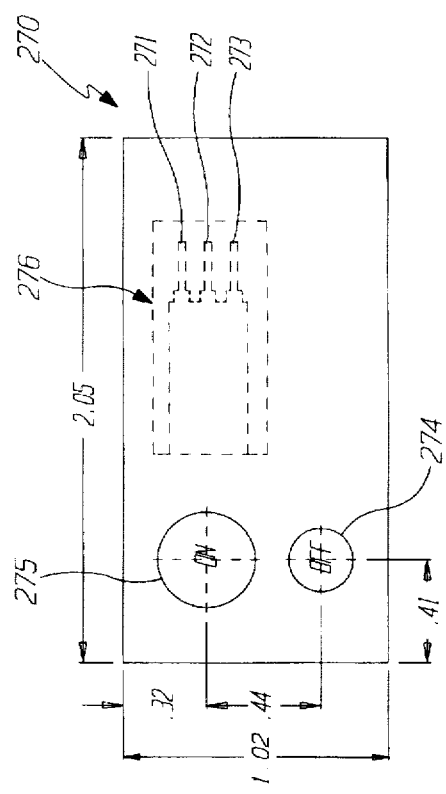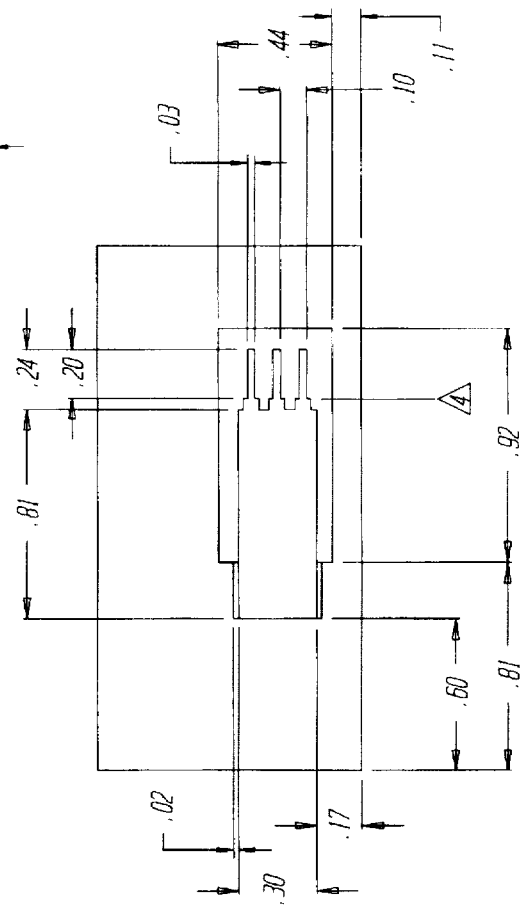

BALLOON CATHETER WITH IMPROVED PRESSURE SOURCE

CROSS-REFERENCE TO RELATED APPLICATIONS

This application is a continuation-in-part of patent application Ser. No. 08/586,514 filed on Jan. 16, 1996, now U.S. Pat. No. 5,695,468 entitled BALLOON CATHETER WITH IMPROVED PRESSURE SOURCE, which is a continuation-in-part of patent application Ser. No. 08/308,025 filed on Sep. 16, 1994 now U.S. Pat. No. 5,545,133, entitled BALLOON CATHETER WITH IMPROVED PRESSURE SOURCE, the entire disclosures of which are hereby incorporated by reference.

FIELD OF THE INVENTION

The present invention generally relates to balloon catheters. More specifically, the present invention relates to balloon dilation catheters used for the treatment of vascular disease. Those skilled in the art will recognize the benefits of applying the present invention to similar fields not discussed herein.

BACKGROUND OF THE INVENTION

A wide variety of therapeutic techniques have been developed to correct or inhibit vascular diseases. Coronary artery disease (CAD), for example, is an adverse condition of the heart in which the blood flow to the heart muscle is partially or totally restricted by occlusive material in the coronary arteries which narrows the blood flow lumen. The occlusive materials deprive portions of the heart muscle of essential oxygenated blood.

CAD may be treated by a surgical technique referred to as coronary artery bypass graft (CABG) surgery. This surgical procedure involves supplementing blood flow to the heart muscle by grafting a non-native conduit such as a saphenous vein graft (SVG) to the heart. A first end of the SVG is connected to the ascending aorta (proximal to the occlusive material) and the other end is connected to the artery distal of the occlusive material. Although this technique has been useful for treating CAD in native coronary arteries, it is not uncommon for occlusive material to form over time in the SVG thereby necessitating additional therapy.

Percutaneous translumenal coronary angioplasty (PTCA) has gained wide acceptance as an effective and less invasive alternative to CABG surgery in certain patient groups. The PTCA procedure involves the use of an angioplasty balloon catheter, several types of which are well known in the art. The balloon catheter is inserted into the body via the femoral artery and navigated to the coronary arteries assisted by a guide catheter and (usually) a guide wire. The balloon is positioned across the restriction in the artery and subsequently inflated. The inflated balloon widens the restriction and restores blood flow to portions of the heart muscle previously deprived of oxygenated blood.

A PTCA balloon catheter is typically about 135 to 150 cm long and has a manifold at its proximal end and a balloon at its distal end. The manifold facilitates connection to an inflation device which is used to inflate and deflate the balloon. A conventional PTCA balloon catheter also includes an inflation lumen extending through its entire length to facilitate the delivery of inflation fluid to and from the balloon. Depending on the type of catheter used, an inflation lumen may be circular in cross section or it may be annular in cross section. Some catheters have an inflation lumen which is circular at the proximal end of the shaft and annular at the distal end of the shaft. Since PTCA catheters are relatively small in profile in order to facilitate navigation through the vascular system, the inflation lumen extending through the shaft is proportionately small. The long length of a typical inflation lumen in combination with its relatively small size create a significant resistance to the flow of inflation fluid. Consequently, the time required to inflate and deflate the balloon is also long. Because flow rates are proportional to pressure, the drag on the inflation fluid is particularly noticeable during balloon deflation when the maximum possible pressure gradient is 14.7 psi. The deflation time is clinically significant because an excessively long deflation time will compromise the treating physician's ability to relieve aschemia and/or reestablish blood flow across the occlusion being dilated. Furthermore, the compliance of the inflation fluid, the inflation device and the entire structure defining the fluid path add to the delay in balloon deflation and inflation. The compliance of the fluid system reduces the immediate responsiveness of the balloon to actuation of the inflation device.

An inflation device is typically capable of inflating to pressures of about 300 psi, and is capable of drawing a near perfect vacuum (perfect vacuum=−14.7psi). An inflation device is usually in the form of a modified 20 cc syringe and typically includes a threaded plunger with a handle and lock mechanism, and a pressure gauge. Due to its size and weight, a typical inflation device is extremely bulky as compared to a PTCA catheter.

Prior art balloon dilation catheters and inflation devices have certain disadvantages which are desirable to overcome. For example, it is desirable to reduce the inflation/deflation time of a balloon catheter and increase the immediate responsiveness of the balloon. This would allow for a more rapid balloon deflation and thus relieve aschemia and other adverse reactions to prolonged balloon inflation. Reducing inflation/deflation time would also allow for more effective use of the pulsating balloon technique. Eliminating a significant amount of the fluid system compliance would allow the treating physician to better "feel" the response of the vascular restriction to the inflation of the balloon. These desirable aspects would improve the treating physician's capabilities to treat CAD.

It is also desirable to eliminate the need to use a bulky inflation device. Eliminating the need for an inflation device would, for example, reduce the number accessory devices needed in a procedure, reduce the number prepping procedures required, reduce the necessary storage space, and reduce the amount of medical waste generated in a procedure. All of these benefits would ultimately save a significant amount of time and expense on behalf of the treating physician, the medical support staff, the hospital and the patient.

SUMMARY OF THE INVENTION

The present invention overcomes the disadvantages of the prior art and provides the desirable features outlined above by eliminating the need for an inflation device and an inflation lumen. In particular, the present invention, inter alia, reduces the drag on inflation fluid and reduces the compliance of the inflation system. The reduction in drag and compliance correlates to an increase in balloon responsiveness which may be clinically significant for the reasons discussed previously. Eliminating the need for an inflation device and an inflation lumen also correlates to savings of time and money.

Broadly stated, the present invention may be described as a balloon catheter which includes a sealed chamber in fluid communication with a distally mounted balloon and a fluid displacement member disposed at least partially within the sealed chamber to displace fluid into or out of the balloon.

Specifically, one embodiment of the present invention is a balloon catheter which includes a long tubular member having a balloon connected to it's distal end. A fluid displacement rod is at least partially and slidably disposed in the tubular member such that the balloon may be expanded when the rod is slid into the tubular member. The rod may include a stop mechanism to inhibit removal of the rod from the tubular member. A seal is connected to the proximal end of the tubular member and disposed about the displacement rod to create a liquid seal between the inside of the tubular member and the displacement rod. The seal may, for example, be an o-ring type seal or a gap tolerance type seal. A pressure gauge may be connected to the proximal end of the elongate tubular member to measure pressure inside the balloon. The balloon catheter may be a fixed wire, an over-the-wire or a single-operator-exchange type balloon catheter.

If the balloon catheter is an over-the-wire or a single-operator-exchange type balloon catheter, a one-way-valve may be connected to the distal end of the tubular member to permit fluid to flow from the guide wire lumen to the interior of the balloon and to prevent fluid from flowing from the interior of the balloon to the guide wire lumen. The valve may be connected to a portion of the tubular member traversing the interior of the balloon and the valve may include an elastomer tube disposed about a hole in the tubular member under the balloon.

The one-way-valve provides a means to prep the catheter (i.e., replace all the air in the catheter with liquid) prior to use in-vivo. One end of the guide wire lumen (e.g., the proximal end) may be plugged and the other end of the guide wire lumen (e.g., the distal end) may be connected to a pressurized liquid source such as a liquid filled syringe to facilitate the prepping process. The pressurized liquid source may be connected to the distal end of the guide wire lumen with a tubular member disposed about the balloon and the tubular member may retain the balloon in a contracted state (sometimes referred to as a balloon protector).

The present invention may also be described as a method of using a balloon catheter including the following steps: (1) providing a balloon catheter (wherein the balloon catheter includes a long tubular member having a balloon connected to it's distal end, a fluid displacement rod at least partially and slidably disposed in the tubular member, the rod including a stop mechanism, and a seal connected to the proximal end of the tubular member and disposed about the displacement rod); (2) inserting the balloon catheter into a vascular system of a patient; (3) positioning the balloon catheter adjacent a treatment site in the vascular system; (4) displacing the rod to at least partially expand the balloon; (5) displacing the rod to at least partially contract the balloon; and (6) withdrawing the balloon catheter from the vascular system.

The present invention may also be described as a method of prepping a balloon catheter including the following steps: (1) providing a balloon catheter (where the balloon catheter includes a long shaft with a lumen disposed therein, a balloon connected to the distal end of the shaft and a one-way-valve also connected to the distal end of the shaft); (2) providing a pressurized fluid source containing fluid therein (such as a fluid filled syringe); (3) connecting the pressurized fluid source to the distal end of the balloon catheter; (4) plugging the proximal end of the balloon catheter; and (5) forcing fluid from the pressurized fluid source into the catheter such that the fluid passes into the tubular member, through the one-way-valve and into the interior of the balloon.

Other aspects and advantages of the present invention can be fully appreciated with a thorough review of the entire specification and drawings. Those skilled in the art will appreciate other advantages not fully described herein. Furthermore, while the disclosure focuses on balloon catheters, those skilled in the art will recognize that the invention may be incorporated into other devices and methods of use without departing from the spirit of the invention.

BRIEF DESCRIPTION OF THE DRAWINGS

FIGS. 2, 3a, 3b, 4a and 4b show specific examples of catheter embodiments utilizing some of the generic features shown in FIG. 1. In particular, FIG. 2 shows a partially-sectioned side view of a fixed wire catheter embodiment. FIGS. 3a and 3b show, respectively, partially-sectioned side views of a side-by-side lumen over-the-wire catheter embodiment and a coaxial over-the-wire catheter embodiment. FIGS. 4a and 4b show partially-sectioned side views of two single-operator-exchange catheter embodiments.

FIG. 5a shows a partially-sectioned side view of a one-way valve incorporated into the distal section of either an over-the-wire or a single-operator-exchange catheter. FIG. 5b shows a detailed view of the one-way valve and FIG. 5c shows a tubular fitting over the distal end of the balloon catheter to facilitate prepping the balloon catheter via the one-way valve.

FIG. 6c shows a first embodiment of a system facilitating prepping a balloon catheter, utilizing a one-way valve as shown in FIGS. 6a and 6b. FIG. 6d shows a detailed view of the passive seal utilized in the prepping system shown in FIG. 6c. FIG. 6e shows a second embodiment of a system facilitating prepping a balloon catheter utilizing a one-way valve as shown in FIGS. 6a and 6b. FIG. 6f shows a detailed view of the active seals used in the prepping system shown in FIG. 6e.

FIGS. 7a and 7b show plan views of two mechanisms which facilitate manipulation of the fluid displacement rod.

FIG. 8 illustrates a cross-sectioned side view of an alternative single-operator-exchange type balloon catheter of the present invention.

FIG. 9 illustrates in more detail a side view of the contrast displacement rod (CDR) incorporated in the balloon catheter shown in FIG. 8.

FIG. 10 illustrates in more detail a cross-sectioned side view of the prep valve incorporated in the balloon catheter shown in FIG. 8.

FIG. 11 illustrates in more detail a cross-sectioned side view of the distal tip of the catheter shown in FIG. 8.

FIGS. 12, 13 and 14 illustrate several cross-sectional views taken along the length of the catheter shown in FIG. 8. In particular, FIG. 12 illustrates a cross-section taken at A—A, FIG. 13 illustrates a cross-section taken at B—B and FIG. 14 illustrates a cross-section taken at C—C.

FIGS. 19 and 20 illustrate the prepping tools used to prepare the catheter shown in FIG. 8 for in-vivo use.

FIGS. 16–18 and 21–27 illustrate in more detail the various components of the manifold assembly shown in FIG. 15.

DETAILED DESCRIPTION OF THE INVENTION

The following detailed description should be read with reference to the drawings in which similar parts in different drawings are numbered the same. The drawings, which are not necessarily to scale, depict exemplary embodiments and are not intended to limit the scope of the invention.

Preferred examples of materials, dimensions, constructions and manufacturing processes are provided for selected parts. All other parts employ materials, dimensions, constructions and manufacturing processes that are well known to those skilled in the field of the invention. Those skilled in the art will recognize that many of the examples provided have suitable alternatives which may also be utilized.

Figure 1:
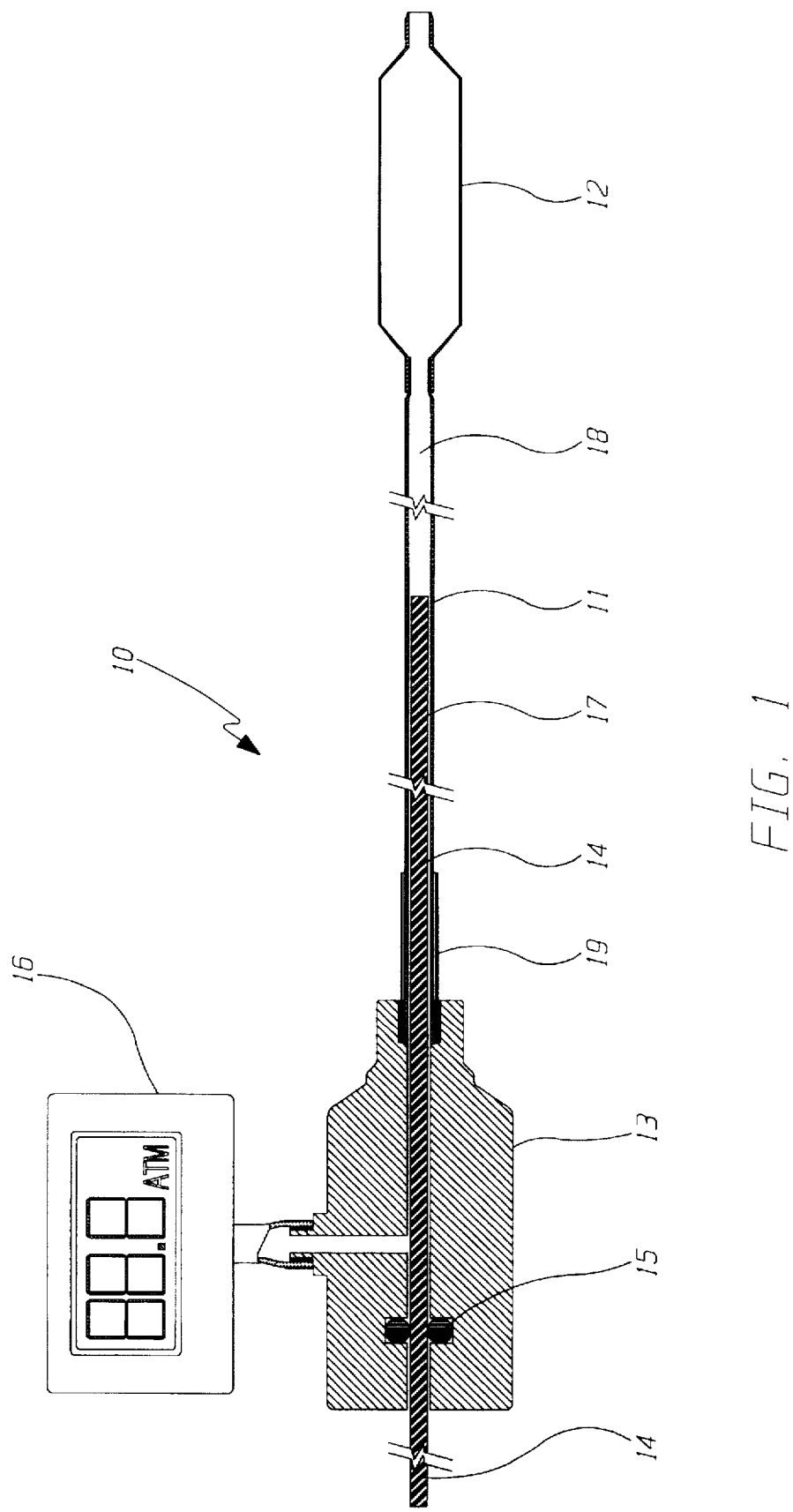
FIG. 1 is a partially-sectioned side view of a generic embodiment of the present invention.

Refer now to FIG. 1 in which a partially-sectioned side view of a generic catheter embodiment 10 is shown. Generic catheter 10 includes an elongate shaft 11 with a balloon 12 connected to its distal end and a manifold 13 connected to its proximal end. A fluid displacement rod 14 is disposed inside the elongate shaft 11 and is longitudinally movable therein. Proximal seal 15 creates a fluid seal between the inside of the elongate shaft 11 and the displacement rod 14 such that longitudinal actuation of displacement rod 14 causes a bolus of liquid 18 to move into or out of the inflatable balloon 12. In particular, when the fluid displacement rod 14 is advanced in the distal direction, the rod 14 displaces liquid bolus 18 into the internal volume of the balloon 12. Further distal advancement of the rod 14 causes the pressure inside the balloon to increase. When the displacement rod 14 is retracted in the proximal direction, liquid bolus 18 exits the balloon and causes the balloon 12 to contract. A static column of fluid 17 links the pressure gauge 16 to the liquid bolus 18 and thus measures the internal pressure of the balloon 12. The term "bolus of liquid" or "liquid bolus" as used in this application is defined as a closed volume of liquid that is relatively large as compared to the static column of fluid 17 between the rod 14 and the inside diameter of the shaft 11.

The generic catheter 10 may take the form of any balloon catheter and may be used in a variety of medical procedures. For example, the generic catheter 10 may take the form of a fixed wire catheter (FIG. 2), an over-the-wire catheter (FIGS. 3a and 3b) or a single-operator-exchange catheter (FIGS. 4a and 4b) and may be used in coronary, peripheral, cerebral and urethral applications. In addition, the generic catheter 10 may incorporate other clinically-significant features such as perfusion or drug delivery capabilities. For the purpose of the following discussion, the exemplary embodiments are directed to a catheter system which is particularly suitable for PTCA procedures. However, with modifications in construction, the generic catheter 10 may be used for other medical applications not fully discussed herein.

The balloon 12 may be constructed in a variety of ways. The material of balloon 10 may be selected from polymers including, but not limited to, polyolefin copolymer, polyester, polyethylene terephthalate, polyethylene, polyether block amide, polyamide, polyimide, nylon, latex and urethane. The balloon 12 may be made by blow-molding a polymer extrusion into the desired shape. A number of ancillary processes may be used to affect the material properties of the balloon 12. For example, the polymer extrusion may be exposed to gamma radiation which alters the polymer infrastructure to provide uniform expansion during blow-molding and additional burst strength when in use. In addition, the molded balloon 12 may be exposed to a low temperature plasma field which alters the surface properties of the balloon 12 to provide enhanced adhesion characteristics. Those skilled in the art will recognize that other materials and manufacturing processes may be used to provide a balloon 12 suitable for use with the present invention.

Similarly, the shaft 11 may be made of several different constructions, materials and dimensions, depending on the performance characteristics desired. The shaft 11 may be made of, for example, an extruded polymer tube, a stainless steel hypotube or a composite material such as stainless steel braid encased in polyimide. To impart different characteristics along the length of the catheter 10, the shaft 11 may incorporate changes in diameter or combine different constructions. For example, the shaft 11 may have a composite proximal section combined with a polymer distal section. Those skilled in the art will recognize that the shaft 11 can take on a wide variety of constructions not fully discussed herein but well known in the art.

Generally, connections between the various polymer components may be made utilizing suitable medical grade adhesives or thermal bonds well known in the art. Connections between metallic components may be made, for example, by utilizing a solder, braze or weld joint.

Manifold 13 may be formed of various polymers such as injection molded polycarbonate. Seal 15 may be made of a conventional sealing material such as silicone rubber and is secured in a recess formed in the manifold 13. The pressure gauge may be secured to the manifold 13 utilizing a threaded connection, an adhesive connection, a thermal weld, or any other suitable means. A strain relief 19 such as a polymer or metallic tube may be secured to the manifold 13 and/or proximal end of the shaft 11 to reduce the tendency of the shaft 11 to kink immediately adjacent the distal end of the manifold 13.

Fluid displacement rod 14 may be in the form of a solid rod, a tube or a combination thereof. For example, fluid displacement rod 14 may be a metallic or polymer rod having a circular cross section. Fluid displacement rod 14 must have a sufficient length to at least partially extend inside the shaft 11 and at least partially extend proximal of the manifold 13. In particular, the fluid displacement rod must have sufficient length to extend proximal of the manifold when the rod 14 is fully displaced in the distal direction. The portion of the rod 14 extending proximal of the manifold 13 provides a handle for the treating physician to grasp and control longitudinal actuation of the rod 14. Preferably, fluid displacement rod 14 extends as far as possible into the shaft 11 to minimize the distance that liquid bolus 18 has to travel and thus increase the responsiveness of the balloon 12. Fluid displacement rod 14 must also have sufficient volume to displace liquid bolus 18 to cause expansion of the balloon 12 when the rod 14 is longitudinally displaced in the distal direction. In addition, fluid displacement rod 14 must have sufficient volume to displace liquid bolus 18 to cause contraction of the balloon 12 when the rod 14 is longitudinally displaced in the proximal direction.

As mentioned previously, pressure gauge 16 is fluidly linked to liquid bolus 18 by way of static fluid column 17.

When balloon 12 is under pressure, liquid bolus 18 exerts a force on the static column of fluid 17 which transfers the force to the pressure gauge 16. The cross-sectional area of static fluid column 17 is preferably minimized to reduce the outside profile of the elongate shaft 11. Minimizing the cross-sectional area of static fluid column 17 does not impede the ability of pressure gauge 16 to measure the pressure of liquid bolus 18 and thus the internal pressure of balloon 12 since the static column of fluid 17 merely transfers force from the liquid bolus 18 to the pressure gauge 16 and accordingly, does not flow. Pressure gauge 16 is preferably a low compliance pressure gauge utilizing a piezoelectric crystal transducer.

In practice, generic catheter 10 is used in a manner somewhat similar to conventional balloon catheters. In particular, the steps associated with inserting the device in-vivo and positioning the balloon across the treatment site are essentially the same as with conventional balloon catheters. However, the steps for prepping the catheter 10 and inflating the catheter 10 are different. Note that the prepping methods and the balloon expansion methods of the present invention are independent. That is to say that the prepping method may be used without the expansion method and vice-versa, without compromising the advantages associated with each method.

Prepping a catheter means to replace all the air in the catheter with a liquid such as saline mixed with radiographic contrast media. The generic catheter 10 may, for example, be prepped by filling the catheter with liquid prior to final packaging (discussed below) or the catheter may be prepped by utilizing the prep methods discussed below with reference FIGS. 5 and 6. These prep methods are exemplary only and those skilled in the art will recognize that other prep methods may also be utilized. After the catheter 10 is prepped, the catheter may be inserted in-vivo and positioned across the treatment site in essentially the same manner as a conventional balloon catheter.

With the catheter 10 in position in-vivo, the balloon 12 may be expanded by longitudinally actuating the displacement rod 14. Longitudinal actuation of the displacement rod 14 is accomplished by pushing the rod distally while holding the manifold 13 and the shaft 11 relatively fixed. Since the proximal seal 15 creates a fluid tight seal between the inside of the elongate shaft 11 and the displacement rod 14, longitudinal actuation of displacement rod 14 in the distal direction causes the bolus of liquid 18 to move into the inflatable balloon 12. Further distal advancement of the rod 14 causes the pressure inside the balloon 12 to increase. Accordingly, the balloon 12 is expanded to the desired size and/or pressure as measured by angiography and/or the pressure gauge 16. The static column of fluid 17 links the pressure gauge 16 to the liquid bolus 18 and allows measurement of the internal pressure of the balloon 12. When desired, the treating physician may contract the balloon by reversing the actuation steps. In particular, when the displacement rod 14 is retracted in the proximal direction, liquid bolus 18 exits the balloon and causes the balloon 12 to contract. After the treatment is complete, the catheter 10 is removed in substantially the same manner as conventional balloon catheters.

It is contemplated that the catheter 10 may be prepped prior to final packaging. In other words, the interior of the catheter 10 would be filled with a liquid after final assembly but before final packaging such that the catheter 10 would be pre-prepped upon removal from the packaging. Since many polymers used to manufacture catheters are semi-permeable to liquid and liquid vapor, it is contemplated that the packaging would also be filled with the same or similar liquid in order to prevent liquid egress from the interior of the catheter. Alternatively, the inside of the packaging may be filled with a dissimilar fluid that is not mixable with the fluid inside the catheter. For example, if the catheter is filled with a water base solution, an oil base solution may be placed in the packaging to retard liquid egress from inside the catheter. A further alternative is contemplated in which the packaging may be filled with a liquid saturated gas at a pressure at equilibrium with the interior of the catheter. Under these conditions, there would be no pressure or saturation gradient causing fluid egress from inside the catheter.

Figure 2:
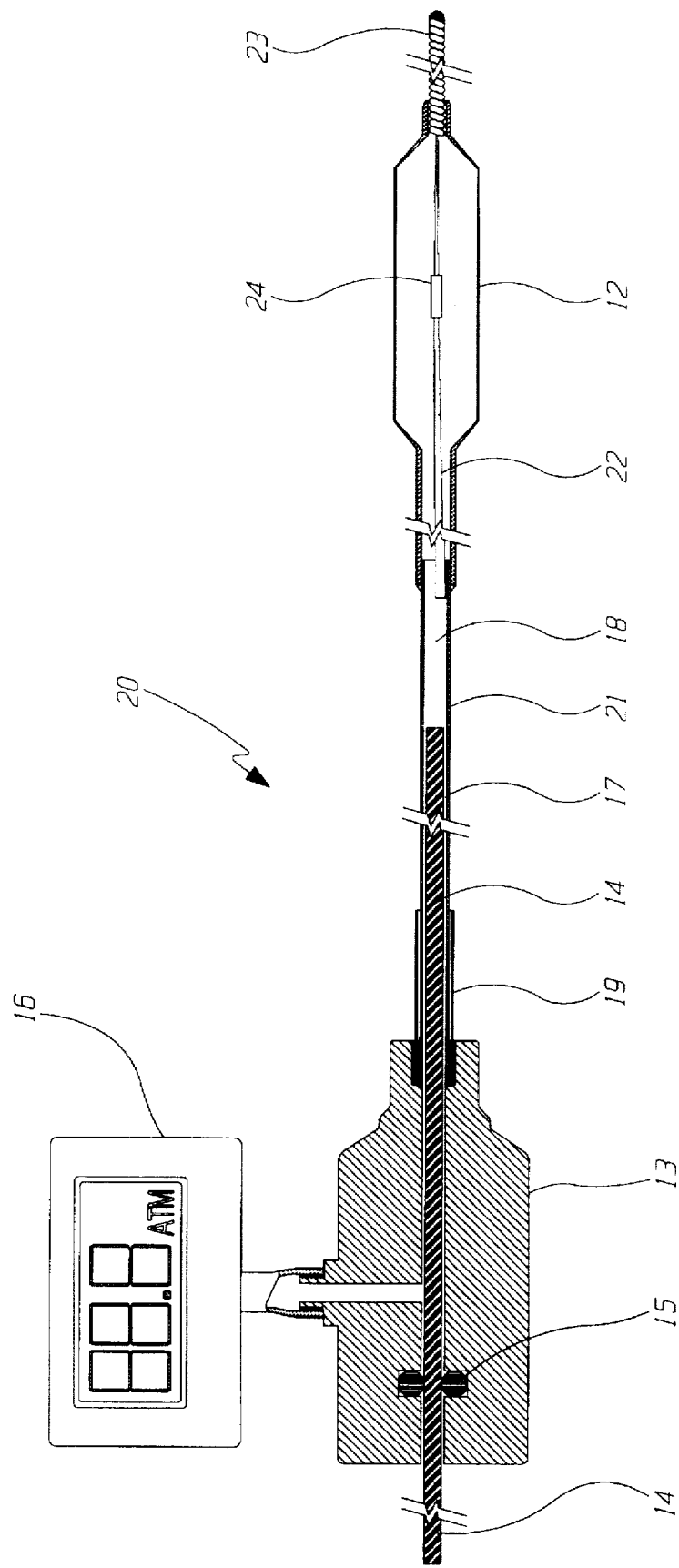

As mentioned previously, generic catheter 10 may take the form of a variety of balloon catheters including a fixed wire type balloon catheter. Refer now to FIG. 2 which shows a partially-sectioned side view of a fixed wire catheter embodiment 20. A more detailed description of a known fixed wire catheter can be found in U.S. Pat. No. 4,943,278 to Euteneuer et al. Fixed wire catheter 20 is similar to generic catheter 10 except for the following differences.

Fixed wire catheter 20 includes an elongate shaft 21 with a balloon 12 sealingly connected to its distal end and a manifold 13 sealingly connected to its proximal end. A strain relief 19 such as a polymer or metallic tube may be secured to the manifold 13 and/or proximal end of the shaft 21 to reduce the tendency of the shaft 21 to kink immediately adjacent the distal end of the manifold 13. A core wire 22 is connected to the distal end of the elongate shaft 21 and extends through the proximal waist of the balloon, traverses the interior of the balloon and terminates with a radiopaque spring tip 23 extending beyond the distal end of the balloon 12. The distal end of the balloon 12 is sealingly connected to the spring tip 23. A radiopaque marker band 24 is secured to the core wire 22 to facilitate radiographic placement of the catheter 20.

Elongate shaft 21 is preferably made of a medical grade metal such as stainless steel or a super elastic alloy such as a Nickel-Titanium alloy having a length of about 44.0 inches, an inside diameter of about 0.014 inches and an outside diameter of about 0.021 inches. Core wire 22 may also be made of a medical grade metal such as stainless steel or a super elastic alloy such as a Nickel-Titanium alloy and may be soldered, brazed or welded to the distal end of the elongate shaft 21. Core wire 22 may have a length of about 14.0 inches and a diameter tapering from about 0.012 inches proximally to about 0.002 inches distally. The spring tip 23 may be coiled about the distal end of the core wire 22 and is preferably made of a radiopaque metal alloy such as an Iridium-Tungsten alloy. Spring tip 23 may be soldered, brazed or welded to the core wire 22 at both ends of the spring coil. Radiopaque marker band 24 is preferably made of Gold, Platinum or Iridium-Tungsten and may be adhesively secured or soldered to core wire 22 at approximately the axial center of the balloon 12.

Figure 3A:
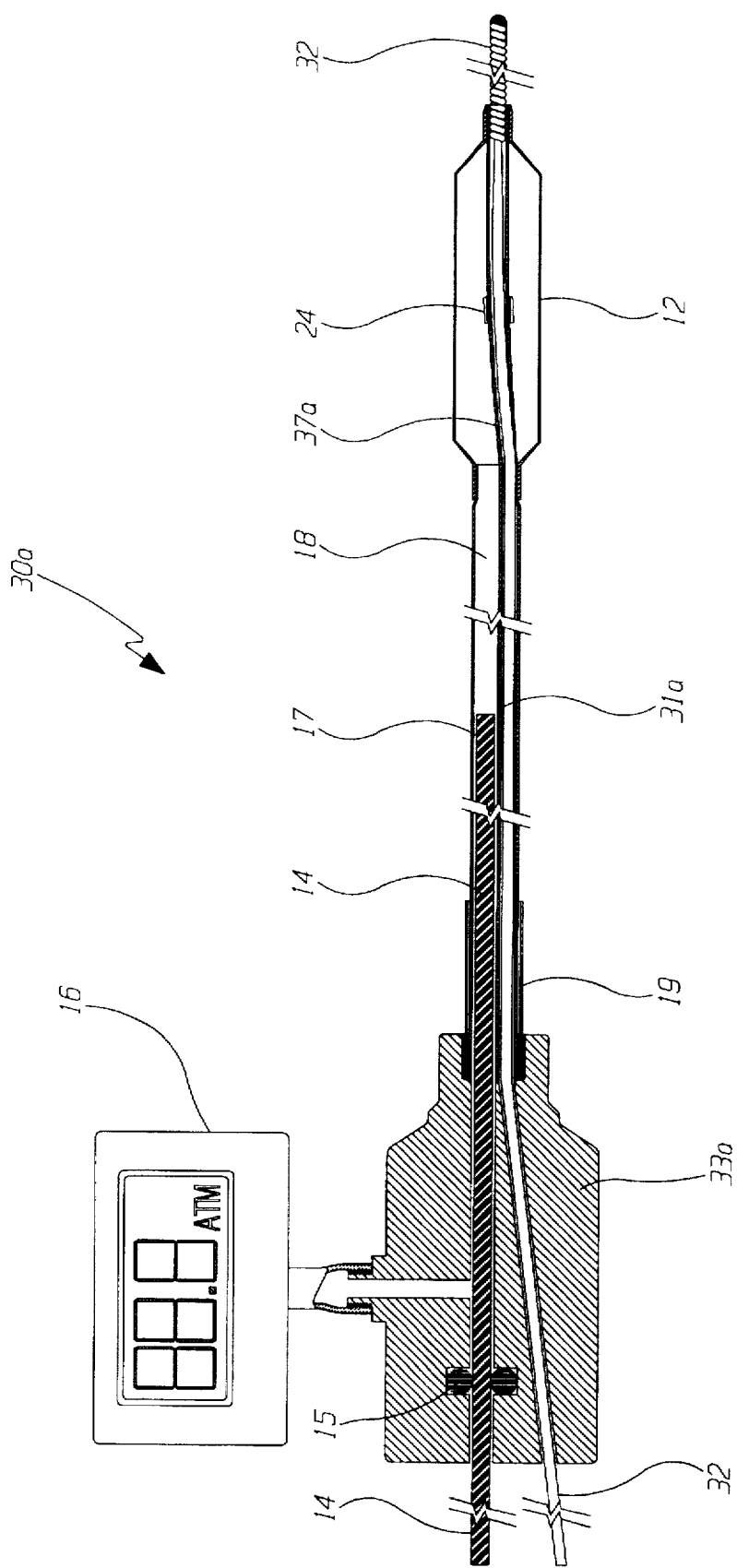
Figure 3B:
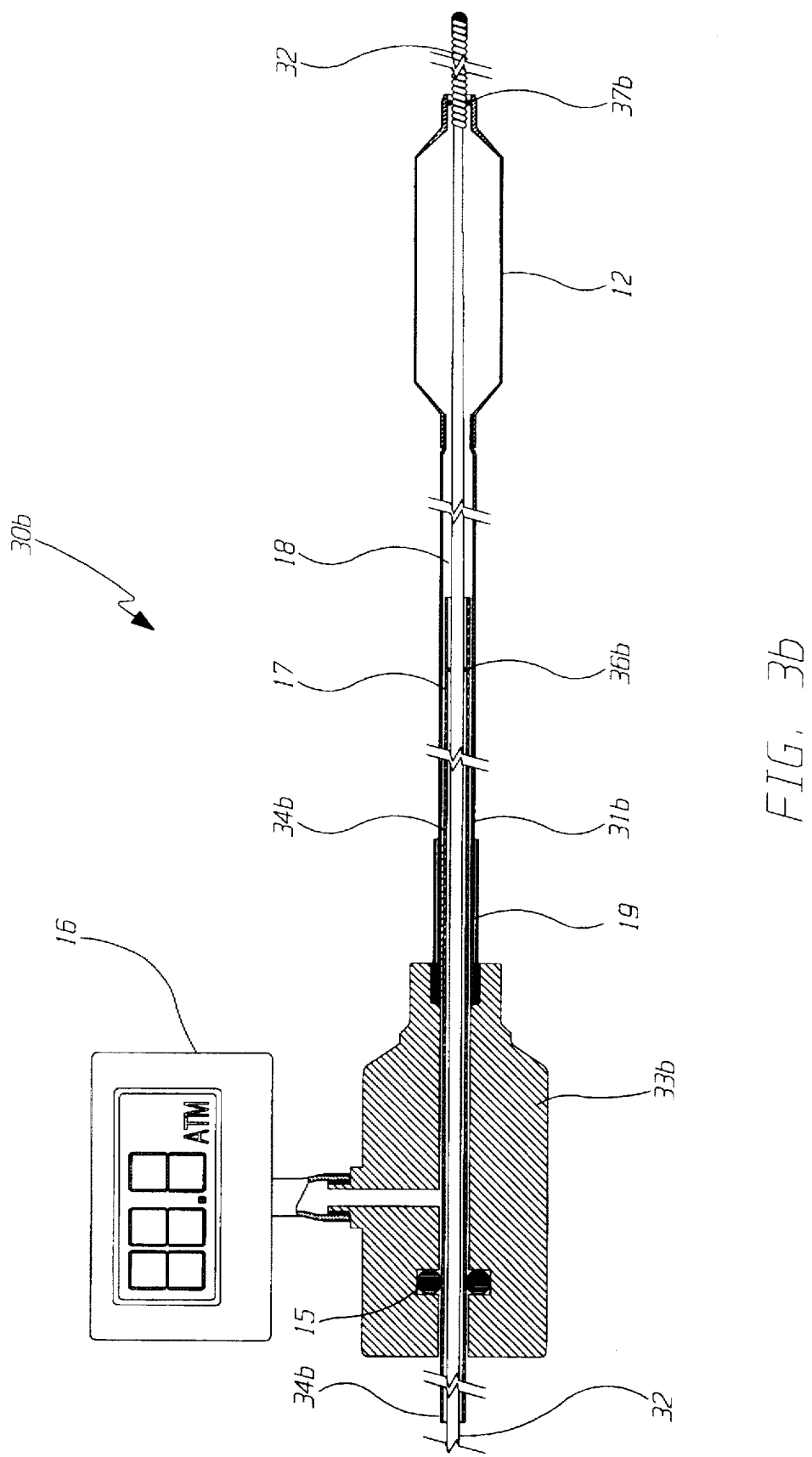

In addition to a fixed wire catheter 20, generic catheter 10 may take the form of an over-the-wire type balloon catheter. Refer now to FIGS. 3a and 3b which show, respectively, partially-sectioned side views of a side-by-side lumen over-the-wire catheter embodiment 30a and a coaxial over-the-wire catheter embodiment 30b. A more detailed description of a known side-by-side lumen over-the-wire catheter can be found in U.S. Pat. No. 5,382,234 to Cornelius et al. and a more detailed description of a known coaxial over-the-wire catheter can be found in U.S. Pat. No. 5,100,381 to Burns. Over-the-wire catheters 30a and 30b are similar to generic catheter 10 except for the following differences.

Side-by-side lumen over-the-wire catheter 30a includes a dual lumen shaft 31a with an inflatable balloon 12 connected to its distal end and a manifold 33a connected to its proximal end. Guide wire 32 passes through manifold 33a, into the dual lumen shaft 31a, through the shaft extension 37a and exits distally of the balloon 12. The distal end of the balloon 12 is sealingly connected to the distal end of the shaft extension 37a and the proximal end of the balloon is sealingly connected to the distal end of the dual lumen shaft 31a. A strain relief 19 such as a polymer or metallic tube may be secured to the manifold 33a and/or the proximal end of the dual lumen shaft 31a to reduce the tendency of the shaft 31a to kink immediately adjacent the distal end of the manifold 33a. A radiopaque marker band 24 may be secured to the shaft extension 37a to facilitate radiographic placement of the catheter 30a.

Dual lumen shaft 31a may be made of a dual lumen extruded polymer or two separate tubes secured together side-by-side. Dual lumen shaft 31a may have a length of about 52.0 inches and an outer diameter of approximately 0.040 inches. Shaft extension 37a may be a partial continuation of the dual lumen shaft 31a or a separate tube secured to the distal end of the dual lumen shaft 31a. Radiopaque marker band 24 is preferably made of Gold, Platinum or Iridium-Tungsten and may be adhesively secured to the shaft extension 37a at approximately the axial center of the balloon 12.

Coaxial over-the-wire catheter 30b includes an elongate shaft 31b with a balloon 12 sealingly connected to its distal end and a manifold 33b sealingly connected to its proximal end. A strain relief 19 such as a polymer or metallic tube may be secured to the manifold 33b and/or the proximal end of the shaft 31b to reduce the tendency of the shaft 31b to kink immediately adjacent the distal end of the manifold 33b. A fluid displacement tube 34b is slidably disposed in elongate shaft 31b. Proximal seal 15 provides a liquid tight seal between the interior of the elongate shaft 31b and the exterior of the displacement tube 34b. A guide wire 32 extends through the interior of the fluid displacement tube 34b, through the distal end of the elongate shaft 31b and exits distally of the balloon 12. Proximal guide wire seal 36b provides a fluid tight seal between the guide wire 32 and the interior of the fluid displacement tube 34b. Distal guide wire seal 37b provides a fluid tight seal between the interior of the balloon 12 and the guide wire 32. With this arrangement of seals 15/36b/37b, longitudinal actuation of displacement tube 34b causes the bolus of liquid 18 to move into or out of the inflatable balloon 12.

Shaft 31b may be formed of a polymer extrusion or composite tube having a length of about 52.0 inches and an outer diameter of about 0.040 inches. Displacement tube 34b may be formed of a reinforced polymer tube having a length of about 50.0 inches, an inner diameter of about 0.018 inches and an outer diameter of about 0.025 inches. Examples of suitable guide wire seals 36b/37b are disclosed in commonly-assigned co-pending patent application Ser. No. 08/443,496 entitled "Single Operator Exchange Perfusion Catheter Having a Distal Catheter Shaft Section" which is fully incorporated herein by reference.

Figure 4B:
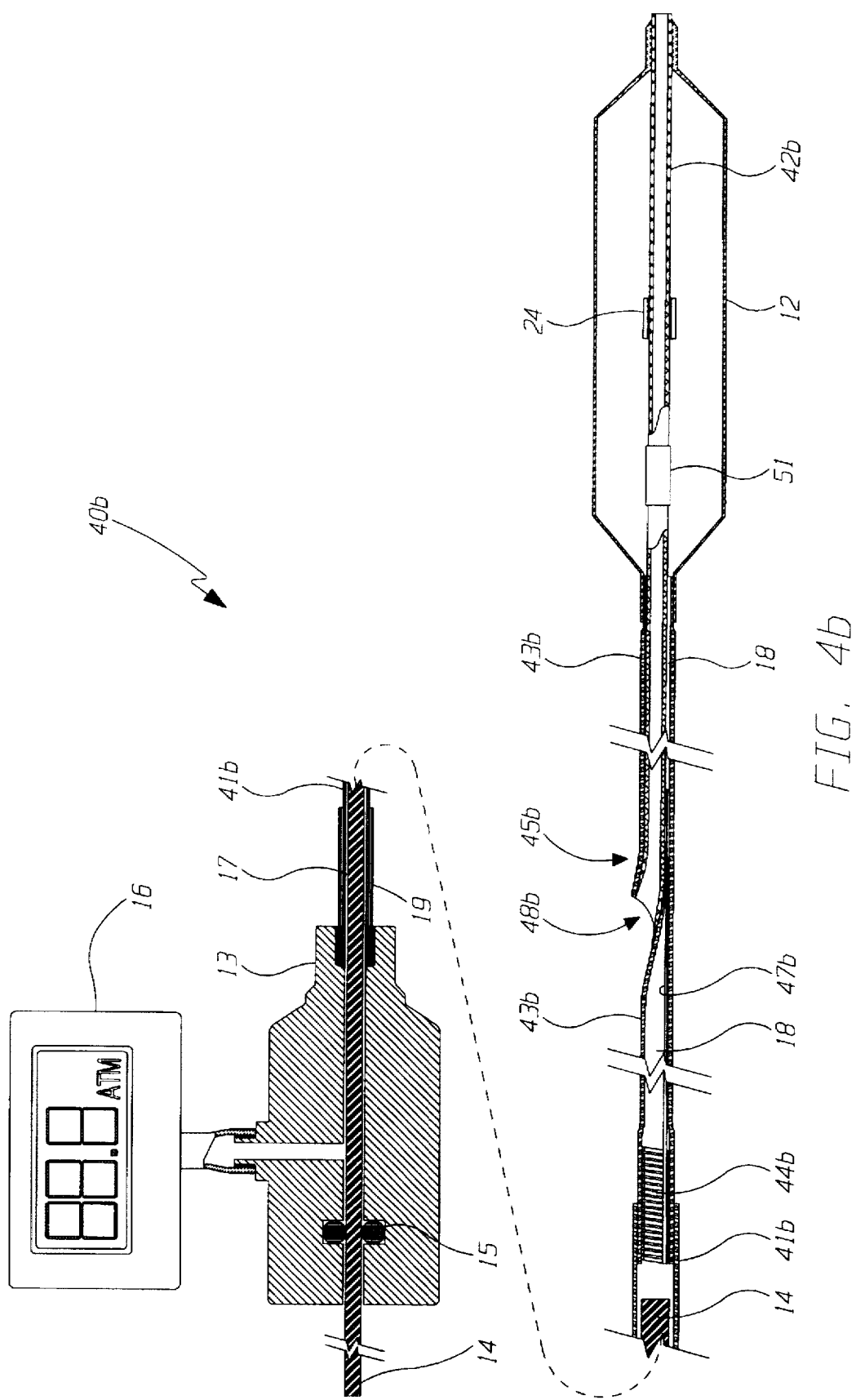

In addition to a fixed wire catheter 20 and an over-the-wire catheters 30a and 30b, generic catheter 10 may take the form of a single-operator-exchange type balloon catheter. Refer now to FIGS. 4a and 4b which show partially-sectioned side views of two single-operator-exchange catheter embodiments. Note that catheter 40a is a generic single-operator-exchange catheter embodiment while catheter 40b is a relatively specific single-operator-exchange catheter embodiment. A more detailed description of a known single-operator-exchange balloon catheter can be found in U.S. Pat. No. 5,156,594 to Keith et al. Single-operator-exchange catheters 40a and 40b are similar to generic catheter 10 except for the following differences.

Single-operator-exchange catheter 40a includes an elongate shaft 41a with a balloon 12 sealingly connected to its distal end and a manifold 13 sealingly connected to its proximal end. A strain relief 19 such as a polymer or metallic tube may be secured to the manifold 13 and/or the proximal end of the shaft 41a to reduce the tendency of the shaft 41a to kink immediately adjacent the distal end of the manifold 13. A guide wire tube 42a has a distal end sealingly connected to the distal end of the balloon and a proximal end defining a proximal guide wire port 48a in communication with the exterior of the catheter 40a and sealingly connected to the elongate shaft 41a. Proximal guide wire port 48a is located at a point substantially distal of the proximal end of the catheter 40a and proximal of the distal end of the catheter 40a. A guide wire (not shown) may traverse the interior of the guide wire tube 42a such that the guide wire enters the proximal guide wire port 48a and exits distally of the balloon 12. A radiopaque marker band 24 may be secured to the guide wire tube 42a to facilitate radiographic placement of the catheter 40a.

Single-operator-exchange catheter 40b includes a proximal shaft section 41b with a manifold 13 connected to its proximal end and a distal shaft section 43b connected to its distal end. A strain relief 19 such as a polymer or metallic tube may be secured to the manifold 13 and/or the proximal end of the shaft 41b to reduce the tendency of the shaft to kink immediately adjacent the distal end of the manifold 13. An additional strain relief 44b may traverse the connection between the proximal shaft 41b and the distal shaft 43b. Strain relief 44b reduces the tendency of the distal shaft 43b to kink immediately adjacent the distal end of the proximal shaft 41b. A core wire 47b has a proximal end rigidly connected to the distal end of the proximal shaft 41b and/or the proximal end of the distal shaft 43b. Core wire 47b transfers longitudinal force from the distal end of the proximal shaft 41b, provides for decreasing diametric stiffness along the length of the distal shaft 43b and acts as a strain relief reducing the propensity of the distal shaft 43b to kink immediately adjacent the crimp section 45b. Guide wire tube 42b is sealingly connected at its distal end to the distal end of the balloon 12. The proximal end of the guide wire tube 42b defines a proximal guide wire port 48b in communication with the exterior of the catheter 40b and sealingly connected to the distal shaft 43b. Proximal guide wire port is located at a point substantially distal of the proximal end of the catheter 40a and preferably about 2.75 inches proximal of the distal end of the catheter 40a. A guide wire (not shown) may traverse the interior of the guide wire tube 42b such that the guide wire enters the proximal guide wire port 48b and exits distally of the balloon 12. A radiopaque marker band 24 may be secured to the guide wire tube 42b to facilitate radiographic placement of the catheter 40b. Optionally, a one-way valve 51 may be connected to the guide wire tube 42b to facilitate prepping the catheter 40b. The incorporation of one-way-valve 51 to facilitate prepping is preferred but not necessary as other suitable prep methods known to those skilled in the art may also be employed. One-way valve 51 and the prepping method are discussed in detail with reference to FIGS. 5a–5c.

Proximal shaft 41b is preferably made of a polyimide-encased stainless steel braid having an inside diameter of approximately 0.0394 inches, an outside diameter of about 0.0466 inches and a length of approximately 44.0 inches. The stainless steel braid embedded in the polyimide preferably has a pick-per-inch ratio ranging from about 50 to about 70. The stainless steel braid is preferably made of woven stainless steel ribbon having a width of approximately 0.005 inches and a height of approximately 0.0007 inches. Manifold 13 may be adhesively secured to the proximal end of the elongate proximal shaft 41b by means of a suitable medical grade adhesive. Manifold 13 is preferably made of injection-molded polycarbonate having an approximately 0.123 inch diameter recess provided for the proximal seal 15 which is preferably made of silicone having an inside diameter of about 0.042 inches and an outside diameter of about 0.142 inches. Pressure gauge 16 preferably incorporates a piezo-electric crystal pressure transducer and a digital readout.

Liquid displacement rod 14 is preferably made of a stainless steel wire surrounded by a Kynar™ tube. The stainless steel wire preferably has a diameter of about 0.019 inches and a length of about 50.0 inches. The tube surrounding the wire preferably has an outside diameter of about 0.038 inches and an inside diameter of about 0.020 inches. When fully actuated in the distal direction, displacement rod 14 preferably may extend to the distal end of the proximal shaft section 41b to minimize the distance liquid bolus 18 has to travel and thus increase the responsiveness of the balloon.

Distal shaft section 43b is preferably made of polyethylene having an outside diameter of about 0.0364 inches tapering to about 0.0335 inches, an inside diameter of about 0.0308 inches tapering to about 0.0277 inches and a length of about 8.0 inches. The proximal end of the distal shaft section 43b may be adhesively secured to the distal end of the proximal shaft segment 41b. Strain relief 44b is preferably made of a stainless steel coil with an outside diameter of about 0.028 inches and a pitch of about 0.068 inches. The stainless steel coil is preferably formed by a coiled ribbon having a width of about 0.019 inches and a height of about 0.003 inches. The core wire 47b is preferably made of stainless steel having a proximal diameter of about 0.012 inches tapering to a distal diameter of about 0.003 inches. The proximal end of the core wire 47b is preferably brazed to the strain relief 44b which in turn is adhesively secured to the inside of the distal shaft segment 43b.

Guide wire tube 42b is preferably made of polyethylene having an outside diameter of about 0.0215 inches, an inside diameter of about 0.0163 inches and a length of about 2.75 inches. The distal end of the guide wire tube 42b is adhesively secured to the distal end of the balloon 12 by a suitable medical grade adhesive. The proximal end of the guide wire tube 42b is preferably thermally bonded to the distal shaft section 43b in a crimped portion 45b of the distal shaft 43b. Balloon 12 is preferably made of a blow-molded polyether-block-amide such as PEBAX™ 7233. The proximal end of the balloon 12 may be adhesively secured to the distal end of the distal shaft segment 43b utilizing a suitable medical grade adhesive. The working portion of the balloon 12 may range in length anywhere from 10 mm to 50 mm and may range in diameter anywhere from 1.0 mm to 10.0 mm.

Refer now to FIGS. 5a–5c which show a partially-sectioned side view of a one-way valve 51 incorporated into the distal section of a balloon catheter such as an over-the-wire or a single-operator-exchange type balloon catheter. One-way-valve 51 may be incorporated into virtually any balloon catheter having a guide wire tube (or similar structure) traversing the interior of the balloon, including some of the balloon catheters discussed previously.

One-way valve 51 may be incorporated into guide wire tube 52 which traverses the interior of the balloon 53a. One-way valve 51 includes an elastic tube 55 disposed about one or more holes 54 in the wall of guide wire tube 52. Elastic tube 55 is preferably made of an elastomer such as Techothane™ 1085A having a length of about 1.2 inches, an inside diameter of about 0.0165 inches and an outside diameter of about 0.023 inches. The elastic tube 55 is preferably centered about two holes 54 formed through one side of the guide wire tube 52 wherein the holes 54 preferably have a diameter of about 0.009 inches. To facilitate prepping, a tubular fitting 56 such as a balloon protector is disposed over folded balloon 53b. A connector 57 such as a luer fitting allows the tubular fitting to be connected to a pressurized fluid source such as a fluid-filled syringe (not shown). Tubular fitting 56 fits snugly about folded balloon 53b such that fluid introduced into the tubular fitting 56 enters into the interior of the guide wire tube 52.

As pressurized fluid enters the guide wire tube 52, elastic tube 55 deflects in an outward direction permitting fluid to flow through holes 54 and into the interior of the catheter and the balloon 53. Elastic tube 55 preferably requires a threshold actuation pressure of greater than one atmosphere of pressure to deflect and permit fluid to flow through holes 54. Having a threshold pressure above one atmosphere allows the balloon 53 to be contracted in a conventional manner (i.e., by pulling a vacuum at the proximal end of the catheter) without drawing any unwanted fluids through the one-way valve 51. Fluid flow from the interior of the balloon 53 to the interior of the guide wire tube 52 is prevented by elastic tube 55 which presses against guide wire tube 52 and forms a seal about holes 54 when the inside pressure of the balloon 53 is greater than the pressure inside the guide wire tube 52. Accordingly, one-way valve 51 permits fluid to flow from the interior of the guide wire tube into the interior of the balloon 53 but does not permit flow from the interior of the balloon 53 to the interior of the guide wire tube 52.

It is contemplated that one-way valve 51 may be located proximal of the balloon if the tubular fitting 56 maintains the balloon 53b in such a contracted state that an insignificant amount of air is trapped inside the balloon 53. In this embodiment, a vacuum source (not shown) such as a vacuum bottle may be connected to the proximal end of the catheter to facilitate filling the catheter shaft and the balloon 53 with liquid. To maximize effectiveness, the vacuum source should be applied prior to introducing pressurized fluid from the syringe.

Figure 6A:
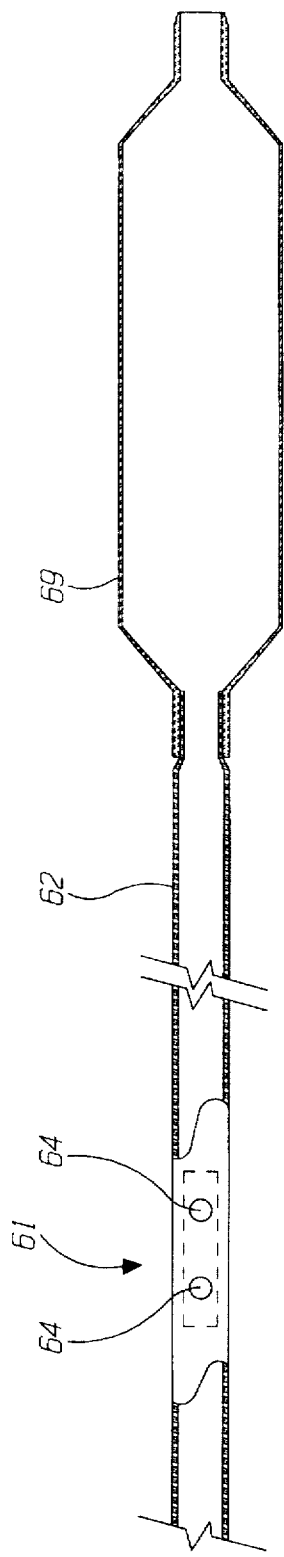
FIG. 6a shows a partially-sectioned side view of the distal section of a generic catheter incorporating a one-way valve proximal of the balloon.

Refer now to FIG. 6a which shows a partially-sectioned side view of the distal section of a balloon catheter incorporating a one-way valve 61 proximal of the balloon. One-way-valve 61 may be incorporated into virtually any balloon catheter in addition to those discussed above. One-way valve 61 operates based on the same principles as one-way valve 51 discussed with reference to FIGS. 5a–5c. One-way valve 61 is incorporated into a shaft 62 proximal of the balloon 69 and includes one or more holes 64 through the wall of the shaft 62. An elastic tube 65 is disposed within the shaft 62 across the holes 64. When the pressure outside the holes 64 is above one atmosphere relative to the pressure inside the shaft 62, the elastic tube 65 deflects in an inward direction and permits flow through the holes 64 to the interior of the shaft 62. When the pressure inside the shaft 62 is greater than the pressure outside the shaft, the elastic tube 65 presses against the inside of the shaft 62 sealing about holes 64 preventing flow from the interior of the shaft 62 to the exterior of the shaft. Accordingly, one-way valve 61 only permits flow from the exterior of the shaft 62 to the interior of the shaft at pressure gradients above one atmosphere.

Figure 6B:
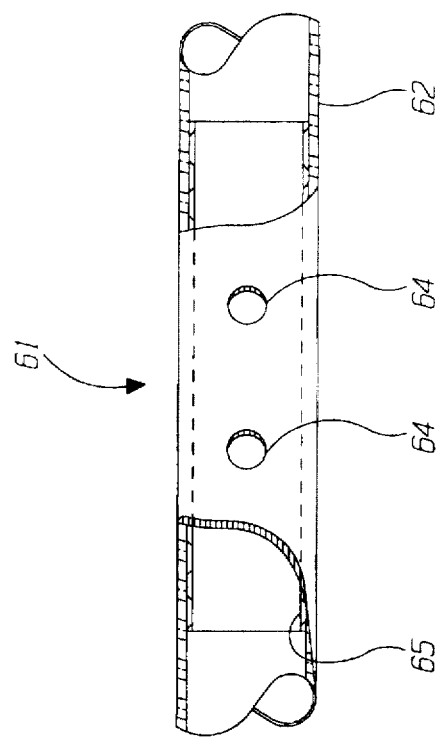
FIG. 6b shows a detailed view of the one-way valve.

Refer now to FIGS. 6c and 6d which show a first embodiment of a system facilitating prepping of a balloon catheter utilizing the one-way valve 61 as shown in FIGS. 6a and 6b. The catheter to be prepped includes an elongate shaft 62 having a manifold 68 connected to its proximal end and a balloon 69 connected to its distal end. The catheter is disposed inside a carrier tube 67 which is conventional for balloon catheter packaging. The distal end of the carrier tube 67 includes a connector 72 to facilitate connection to a pressurized fluid source such as a liquid-filled syringe 63. A passive seal 71 such as an O-ring seal is connected to the inside of the carrier tube 67 at a point proximal of the one-way valve 61. Accordingly, when pressurized fluid is introduced by way of the syringe 63, fluid passes through the valve holes 64 and into the interior of the catheter shaft 62. A vacuum source 66 such as a vacuum bottle may be connected to the manifold 68 to facilitate filling the catheter shaft 62 and the balloon 69 with liquid. To maximize effectiveness, vacuum source 66 applies a vacuum to the interior of the catheter shaft 62 prior to introducing pressurized fluid from the syringe 63.

Refer now to FIGS. 6e and 6f which show a second embodiment of a system facilitating prepping of a balloon catheter utilizing the one-way valve 61 as shown in FIGS. 6a and 6b. As discussed with reference to FIGS. 6c and 6d, catheter shaft 62 includes a manifold 68 connected to its proximal end and a balloon 69 connected to its distal end. A vacuum source 66 may be connected to the manifold 68 to facilitate prepping as discussed previously. A syringe 63 is connected to the carrier tube 67 utilizing connector tubes 84. Connector tubes 84 are in turn connected to active seals 81 and 82 located inside the carrier tube 67. When pressurized fluid is introduced by the syringe 63 through the connector tubes 84, active seals 81 and 82 fluidly seal on either side of the one-way valve 61. In particular, active seals 81 and 82 comprise oppositely-facing balloons which, upon inflation, seal about the catheter shaft 62 and the interior of the carrier tube 67. A small hole 83 is placed in one of the active seals 81 or 82 such that fluid under pressure from syringe 63 seeps into the chamber defined between active seals 81 and 82. The fluid which seeps from hole 83 is under sufficient pressure to deflect the elastic tube 65 and cause fluid to flow into the holes 64 and into the interior of the shaft 62, thus displacing air inside the catheter shaft 62 with liquid from the pressurized fluid source 63.

Refer now to FIGS. 7a and 7b which show plan views of two mechanisms which facilitate manipulation of the fluid displacement rod 14. In FIG. 7a, displacement mechanism 71a includes an engagement member 72a which engages the fluid displacement rod 14 when moved in the distal direction and accordingly causes fluid displacement rod 14 to also move in the distal direction. When moved in the proximal direction, engagement member 72a disengages the fluid displacement rod 14 and slides thereon. Manifold 13 (which is connected to the proximal end of the shaft 11) may include a thumb ring 73a and engagement member 72a may includes grooves 74a for receiving fingers such that the engagement member 72a may be grasped with middle and first fingers and the manifold may be grasped with the thumb. Accordingly, simple contraction of the hand causes the engagement member 72a to move distally relative to the manifold 13 and thus cause fluid displacement rod to move distally effecting expansion of the balloon. A metal tube 75a may be secured over the proximal portion of the rod 14 to add integrity to the displacement mechanism and avoid damage to the rod 14.

Refer now to FIG. 7b which shows displacement mechanism 71b which facilitates advancement of fluid displacement rod 14. Displacement mechanism 71b includes an engagement member 72b which incorporates a push button lock mechanism 73b. Push button lock mechanism 73b is normally locked onto the fluid displacement rod 14 such that depression of the push button on the lock mechanism 73b causes disengagement of the fluid displacement rod 14. A proximal portion 74b of the fluid displacement rod 14 is threaded and is engaged by threads (not shown) inside manifold 13. Accordingly, the fluid displacement rod 14 is manually displaced in the distal direction with the push button on the lock mechanism 73b fully depressed (i.e., disengaged). Once an initial pressure is reached inside the balloon, the push button on the lock mechanism 73b is released, thus engaging fluid displacement rod 14 and the assembly 72b/14 is rotated, causing advancement of the fluid displacement rod by virtue of threaded portion 74b engaging the threads inside manifold 13. Accordingly rotation of the assembly 14/72b advances the rod 14 to cause the pressure inside the balloon to increase.

Refer now to FIG. 8 which illustrates a cross-sectioned side view of an alternative single-operator-exchange type balloon catheter 80. The design and use of alternative catheter 80 is similar to catheter 40b illustrated in FIG. 4b except as described hereinafter.

Figure 15:
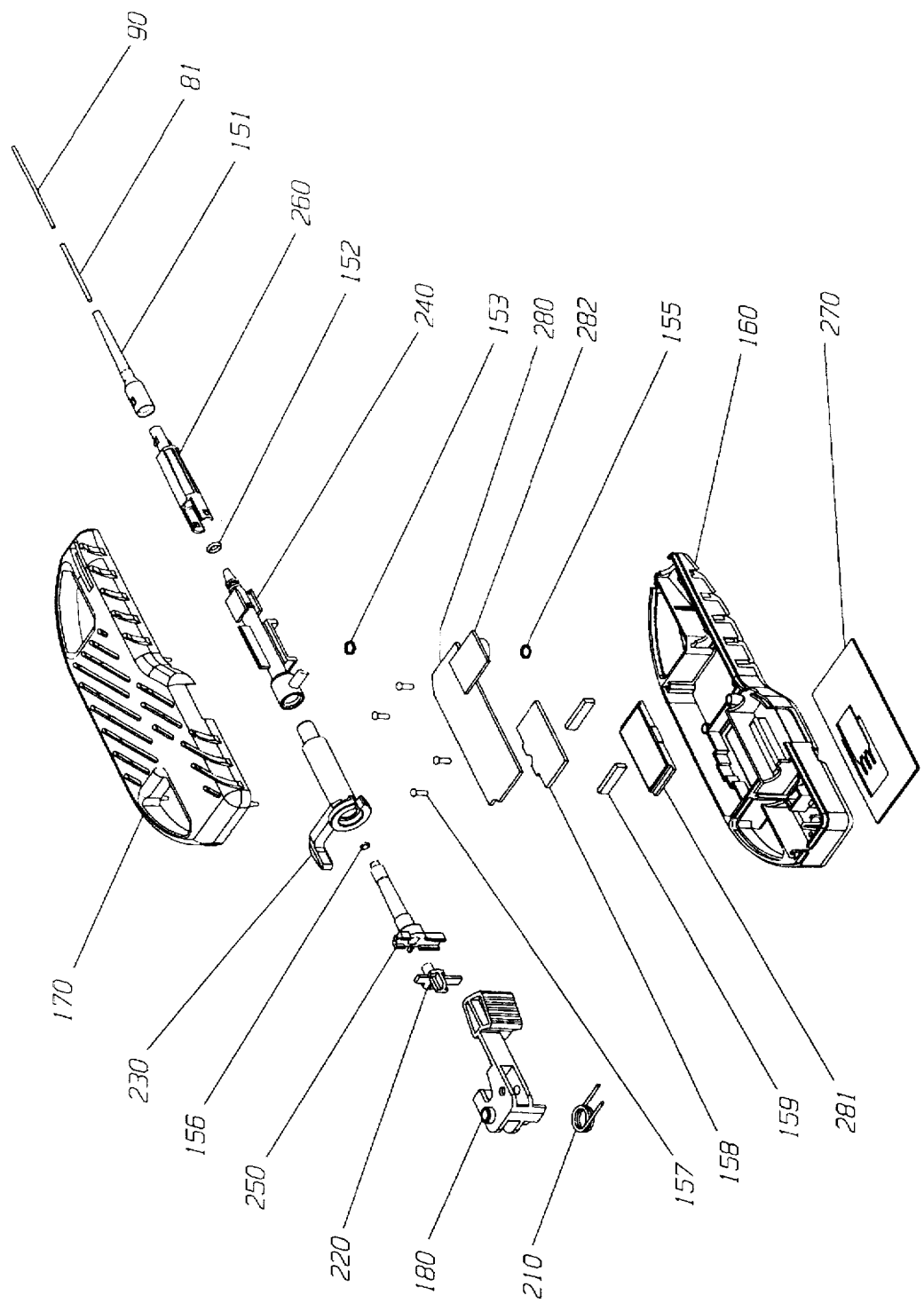
FIG. 15 illustrates an exploded isometric view of a manifold assembly for connection to the catheter shown in FIG. 8.

Catheter 80 includes a proximal shaft portion 81 with a distal outer 82 connected to its distal end. The proximal shaft portion and the distal outer define a sealed chamber 124 as best seen in FIG. 12. The distal end of the distal outer 82 is connected to the proximal end of the balloon 84. The sealed chamber is closed at it's distal end by a connection between the balloon 84 and the distal inner 83 at the distal tip 110 of the catheter 80. The distal inner 83, which defines a guide wire lumen 131 as best seen in FIG. 13, is sealably connected at it's proximal end to the distal outer 82, preferably utilizing a thermal bond 86. A contrast displacement rod (CDR) 90 is movably positioned in the sealed chamber 124. The sealed chamber 124 is closed at it's proximal end by the CDR seal 156 as best seen in FIG. 15 which permits longitudinal movement of the CDR 90 while maintaining a fluid tight seal around the CDR 90.

When a liquid, such as a solution of saline and radiopaque contrast media, is disposed in the sealed chamber 124, longitudinal movement of the CDR 90 causes a bolus of liquid to either inflate or deflate the balloon. In particular, when the CDR 90 is displaced in the distal direction, a bolus of liquid is displaced by the CDR 90 into the balloon 84, thus inflating the balloon 84. Similarly, when the CDR 90 is displaced in the proximal direction, a bolus of liquid is drawn from the balloon 84, thus deflating the balloon 84. This configuration eliminates the need for an inflation lumen as required for conventional balloon catheters.

Continuing to refer to FIG. 8, one or more radiopaque marker bands 85 may be mounted on the distal inner 83 to facilitate radiographic placement of the catheter in-vivo. A tapered core wire 87 is connected at it's proximal end to the proximal end of the distal outer 82 and the distal end of the proximal shaft 81 utilizing a collar 88. The core wire 87 reduces the tendency of the distal outer 82 to kink at the guide wire exit port, i.e., the proximal end of the distal inner 83. The core wire 87 also serves to transmit forces to the distal end of the catheter 80 to facilitate navigation through the coronary vasculature.

A series of shaft markers 89 may be incorporated onto the shaft 81. The shaft markers correlate the position of the catheter 80 in-vivo relative to the guide catheter into which the catheter 80 is inserted. Preferably, shaft markers 89 are positioned at 90 cm and 100 cm from the distal tip 110 of the catheter 80. The shaft markers 89 may be any suitable non-toxic permanent ink or paint applied to the proximal shaft 81.

The proximal shaft section 81 is preferably formed of a polyimide encased stainless steel braid to provide sufficient kink resistance and stiffness to navigate the coronary vasculature. The proximal shaft 81, which houses a portion of the CDR 90, has an inside diameter of about 0.035 to 0.043 inches and an outside diameter of about 0.044 to 0.049 inches, depending in part on the size of the balloon 84 employed. The length of the proximal shaft section 81 is preferably about 44.0 inches.

The distal outer 82 is preferably formed of clear high density polyethylene and is adhesively secured inside the distal end of the proximal shaft 81 and adhesively bonded to the proximal waist of the balloon 84. The distal outer 82 may have a proximal outside diameter of about 0.033 to 0.040 tapering to a distal outside diameter of about 0.033 inches, an inside diameter of about 0.027 inches and a length of about 11.8 to 12.4 inches, depending in part on the size of the balloon 84 employed.

The distal inner 83 is preferably formed of a colored high density polyethylene with it's proximal end thermally bonded at a midpoint along the distal outer 82 and it's distal end adhesively bonded to the distal waist of the balloon 84. The distal inner 83 may have an inside diameter of about 0.016 inches to accommodate a 0.014 inch diameter guide wire and an outside diameter of about 0.021 inches to define an annular space with the inside of the distal outer 82. The distal inner is preferably about 7 cm long but may range in length from about 1.0 to 12.0 inches depending on the desired guide wire lumen 131 length for single-operator-exchange purposes. The proximal end of the inner 83 is preferably skived at a 20° angle to facilitate smooth movement of the guide wire (not shown).

The balloon is preferably formed of an blow-molded polymer tube such as poly-ether-block-amide (e.g., PEBAX™ 7033), irradiated polyolefin copolymer, HDPE, PET or other suitable material. The balloon may have a working diameter ranging from about 1.5 mm to 4.0 mm or more and a working length of about 10 mm to 40 mm or more depending on the size of the vasculature being treated. The balloon 84 may be secured at it's ends with a suitable adhesive such as HB Fuller 3507 urethane adhesive.

The marker bands 85 may be formed of a variety of radiopaque materials such as gold or an alloy thereof. The marker bands 85 may have an inside diameter of about 0.023 inches, a wall thickness of about 0.0015 inches and a length of about 0.051 inches. The marker bands 85 may be centered along the length of the balloon 84 and/or may be aligned with the ends of the working area of the balloon 84.

The core wire is preferably formed of 304 stainless steel and has a proximal and distal taper. The proximal taper provides a smooth transition from the proximal shaft section 81 and the distal taper provides a smooth transition to the distal inner 83 and outer 84 across the guide wire port. The core wire has a maximum outside diameter of about 0.012 inches tapering proximally for a length of 1.0 inches to a diameter of about 0.006 inches and tapering distally for a length of 11.3 inches to a diameter of about 0.003 inches, resulting in an overall length of about 12.3 inches. The core wire 87 is secured to the proximal end of the distal outer 82 and the distal end of the proximal shaft 81 by collar 88 which is formed of 304 stainless steel. In particular, the proximal end of the distal outer 82 is adhesively secured to the distal end of the proximal shaft 81. The collar 88 is adhesively connected to the distal outer 82 and the collar 88 is resistively welded to the core wire 87. The distal end of the core wire 87 terminates adjacent the proximal end of the prep valve 100 and is preferably not secured.

Now refer to FIG. 9 which illustrates in more detail the contrast displacement rod (CDR) 90 which is disposed in the sealed chamber 124 of balloon catheter 80 shown in FIG. 8. The CDR 90 includes a core wire 91 onto which a proximal sheath 92 and a distal sheath 93 are mounted. A distal portion 94 is heat treated to impart additional flexibility to the core 91. The proximal sheath 92 is bonded and back-filled at it's proximal end 95a and distal end to the core 91 with a suitable adhesive such as HB Fuller 3507 urethane adhesive. Similarly, the distal sheath is bonded and back-filled at it's proximal end 95c and distal end to the core 91 with a suitable adhesive such as HB Fuller 3507 urethane adhesive. An ink marker 98 is placed on the proximal sheath 92 to denote the location of the CDR 90 with respect to the manifold during prep.

A stop wire 96 is secured to the core 91 between the proximal sheath 92 and the distal sheath 93. The stop wire 96 is spring biased approximately 12.50° away from the CDR 90 such that it engages the distal cone of the manifold body 240 (shown in FIGS. 15 and 24) when the CDR 90 is retracted and thereby prevents the CDR 90 from being accidentally removed from the catheter 80. The stop wire 96 may be elastically bent toward the CDR 90 to facilitate putting it into the manifold assembly 150 and catheter 80. Those skilled in the art will recognize that other suitable stop mechanisms may be employed to serve the same purpose. For example, a collar having an outside diameter larger than the CDR 90 and larger than the hole in the manifold body 240 may be secured to the CDR 90. This collar would prevent the CDR 90 from being retracted past the point where the collar would engage the distal end of the manifold body 240. Another alternative would be to incorporate a notch in the CDR 90 such that a mating catch lever mounted to the manifold body 240 would engage the notch and prevent unintentional removal of the CDR 90.

The core wire 91 is preferably formed of a superelastic NiTi alloy having a diameter of about 0.021 inches and a length of about 50.0 inches. As mentioned previously, the distal portion 94 is heat treated to impart additional flexibility to the core 91.

The proximal sheath 92 may be formed of a low friction polymer such as a fluoropolymer, preferably KYNAR 2850 having a length of about 23 inches to 36 inches, an inside diameter of about 0.022 to 0.023 inches, and an outside diameter of about 0.033 inches to 0.040 inches. The distal sheath 93 may also be formed of a low friction polymer such as a fluoropolymer, preferably KYNAR 2850. The distal sheath preferably has an inside diameter of about 0.022 to 0.023 inches, an outside diameter of about 0.030 inches to 0.037 inches and a length of about 12.7 inches to about 25.7 inches.

The stop wire 96 is secured to the core 91 by welding or brazing the stop wire 96 to a stainless steel collar 97. The collar 97 is in turn adhesively bonded to the core 91 and the distal end of the collar 97 is adhesively back-filled to provide a smooth transition. The stop wire 96 is positioned approximately 23.5 to 44.5 inches from the proximal end of the CDR 90 depending in part on the size of the balloon 84 to be inflated. The stop wire 96 is preferably formed of 304 stainless steel having a diameter of about 0.007 inches and an exposed length of about 0.30 inches. The distal end of the stop wire 96 is formed into a blunt ball shape to avoid abrading or puncturing parts of the catheter 80.

Refer now to FIG. 10 which illustrates cross-sectioned side view of the prep valve 100. The design and function of prep valve 100 is the same as one-way valve 51 discussed with reference to FIGS. 5a, 5b and 5c except as described hereinafter. The prep valve 100 permits inflation liquid (e.g., a solution of saline and radiopaque contrast media) to pass from the guide wire lumen 131 and into the sealed chamber 124.

Prep valve 100 is positioned adjacent the proximal waist of the balloon 84 on the inner shaft 83. The valve 100 includes a valve sleeve 101 positioned over one or more holes 102 in the inner shaft 83. The valve sleeve may be adhesively secured to the inner shaft at it's proximal end 103 using a suitable adhesive such as HB Fuller 3507 urethane adhesive.

The sleeve 101 is preferably formed of an elastomer such as Techothane 1095A and has a relaxed inside diameter of about 0.0165 inches, a relaxed outside diameter of about 0.0215 inches and a length of about 6.0 mm. The sleeve 101 is preferably positioned over hole 102 such that the center of the hole 102 is about 2.0 mm from the distal edge of the sleeve 101. Preferably one hole 102 is utilized having a diameter of about 0.007 and may be formed by a punching or drilling process.

Refer now to FIG. 11 which shows a cross-sectioned side view of the distal tip 110. At the distal tip 110, the distal waist of the balloon 84 is adhesively bonded and back-filled 111 to the distal end of the inner shaft 83 with a set back of about 1.25 mm to provide a relatively a traumatic tip. The distal edge 112 of the inner shaft 83 is preferably broken or tapered to provide a smooth transition from the guide wire to the distal tip 110.

With reference now to FIG. 12 which shows a cross-section 120 taken at A—A in FIG. 8, the arrangement of parts 81, 82, 88, 87 and the sealed chamber 124 are more visible. The core wire 87 is resistively welded 123 to the collar 88 which is bonded to the distal outer shaft 82 with an adhesive 121 such as cyanoacrylate. The distal outer shaft 82, in turn, is bonded to the proximal shaft 81 with an adhesive 122 such as HB Fuller 2205 urethane adhesive.

Refer now to FIG. 13 which illustrates a cross-section 130 taken at B—B in FIG. 8. Cross-section 130 shows how the distal inner shaft 83 exits the distal outer shaft 82. Initially, a hole is formed in the outer shaft 82 and the inner shaft 82 is pulled therethrough. A round mandrel is positioned in the inner 83 and a crescent mandrel is positioned in the outer shaft 82 across the bond site to maintain the guide wire lumen 131 and the sealed chamber 124. With the mandrels in place, a thermal bond is formed between the inner shaft 83 and the outer shaft 82 so as to form a fluid seal around the inner shaft 83. The inner shaft 83 is then skived at a 20° angle and the resulting cross-section 130 is complete.

Refer now to FIG. 14 which shows a cross-section 140 taken at C—C in FIG. 8. Cross-section 140 illustrates the elastomeric sleeve 101 disposed over the hole 102 in the distal inner shaft 83 which defines the guide wire lumen 131. Also apparent from the cross-section 140 is the distal waist of the balloon 84 secured to the distal end of the distal outer shaft 82.

Refer now to FIG. 15 which shows an exploded isometric view of the manifold assembly 150 for connection to the catheter 80 shown in FIG. 8. The manifold assembly 150, which may be used is conjunction with other catheters described herein, facilitates prepping the catheter 80, controlling the position of the CDR 90, monitoring the pressure inside the balloon 84 and manipulating the catheter 80 in-vivo.

The manifold assembly 150, which is illustrated upside down to reflect the order of assembly more accurately, includes a case top 160 which is an external shell that houses the internal components and provides mechanical support for assembly of the electronic components. The case top 160 is also the land area for a membrane switch panel 270 mounted on it's exterior. Preferably, the case top 160 is made of injection molded black ABS plastic. A detailed view of the case top 160 is illustrated in FIGS. 16a–16c.

The case bottom 170 is also a part of the external shell that houses the components. The case bottom 170 mates with and is connected to the case top 160 utilizing six press pins 157. The case bottom 170 has a series of elongate openings 171 that allow fluid (gas and liquid) to freely enter and exit the manifold assembly 150. The case bottom 170 is preferably made of black ABS plastic by an injection molding process. A detailed view of the case bottom 170 is illustrated in FIGS. 17a–17c.

The distal cap 260 provides the connection between the catheter 80 and the manifold assembly 150. In particular, the manifold assembly 150 is connected to the catheter 80 by adhesively bonding the proximal shaft 81 to the distal cap 260. The cap 260 allows the catheter 80 to be manufactured independently of the manifold assembly 150, wherein the final step in manufacturing is to snap the distal cap to 60 to the manifold body 240. Preferably, the distal cap is made of injection molded orange polycarbonate. A detailed view of the distal cap 260 is illustrated in FIGS. 26a–26g.

A strain relief 151 is snap-fit onto the distal cap 260. The strain relief 151 reduces the tendency of the proximal shaft 81 to kink immediately adjacent the distal end of the distal cap 260. The strain relief is preferably made of injection molded black urethane.

The manifold body 240 has three distinct functions, namely to catch the stop wire 96, fluidly connect the interior 124 of the catheter 80 to the pressure sensor 282, and provide an exit port 244 for prepping the catheter 80. Specifically, the manifold body 240 includes a distal cone 243 that catches the CDR stop wire 96. This prevents accidental withdrawal of the CDR 90 during a procedure. An O-ring 152 between the manifold body 240 and the distal cap 260 creates a fluid tight seal therebetween. The manifold body 240 snaps into the case top 160 capturing another O-ring 153 on the pressure sensor face 282. O-ring 153 provides a sealed interface between the interior 124 of the catheter 80 and the sensor 282. Finally, the manifold body 240 provides an exit port or the prepping vent 244 which is operated by vent lever 230. The manifold body 240 is preferably made of an injection molded clear polycarbonate. A more detailed view of the manifold body 240 is illustrated in FIGS. 24a–24g which show distal cone 243, exit port 244 and a recess 242 for the vent lever 230.

The vent lever 230 includes an internal cylinder 232 which fits into the recess 242 of the manifold body 240 to provide a rotating prepping valve which operates similar to a conventional stop-cock valve. The vent lever also includes a lever portion 231 to facilitate actuating the valve. The interior lumen of the vent lever 230 houses an O-ring 156 that seals about the CDR 90. The vent lever 230 interfaces with back-up bushing 250 to hold the CDR O-ring 156 in position. The vent lever 230 is preferably made of red injection molded polyethylene. A more detailed view of the vent lever 230 is illustrated in FIGS. 23a–23f and a more detailed view of the back-up bushing is illustrated in FIGS. 25a–25d.

Figure 21B:
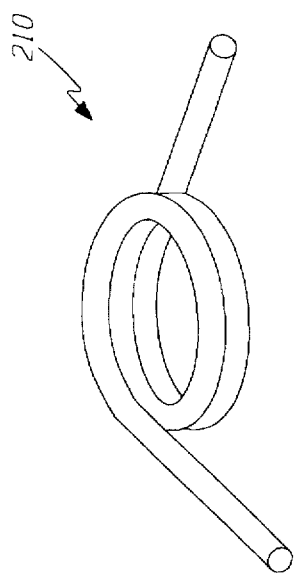
Figure 21A:
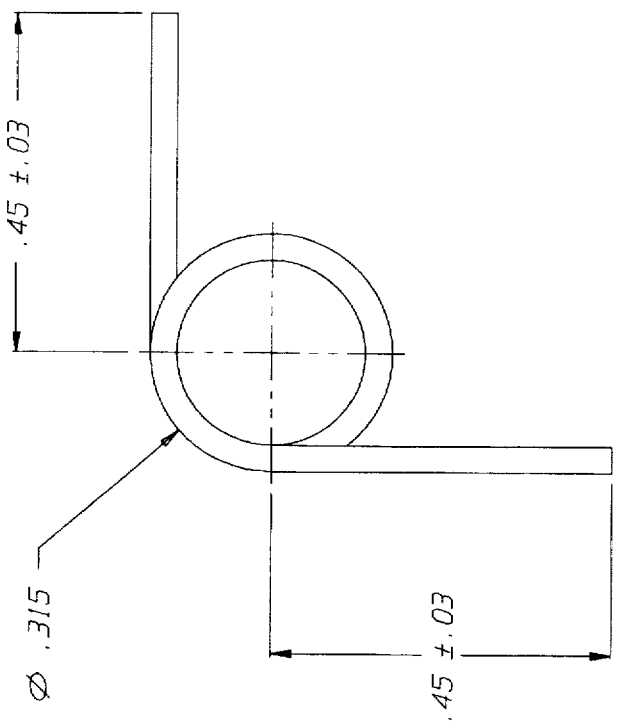
Figure 21C:
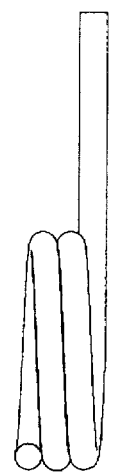
Figure 25B:
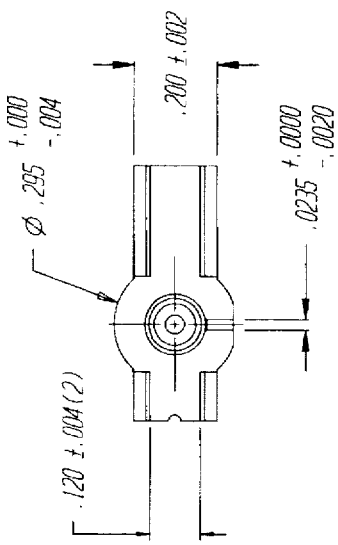
Figure 25D:
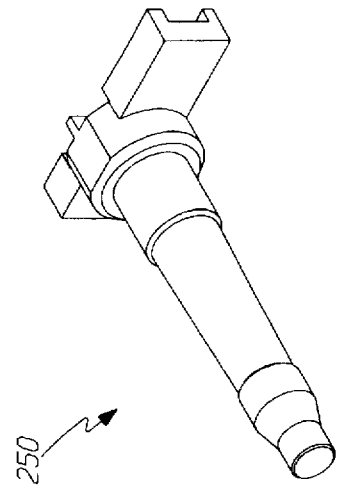
Figure 25A:
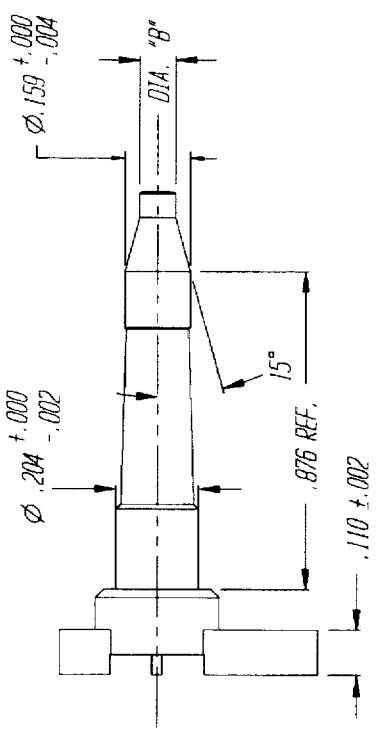
Figure 25C:
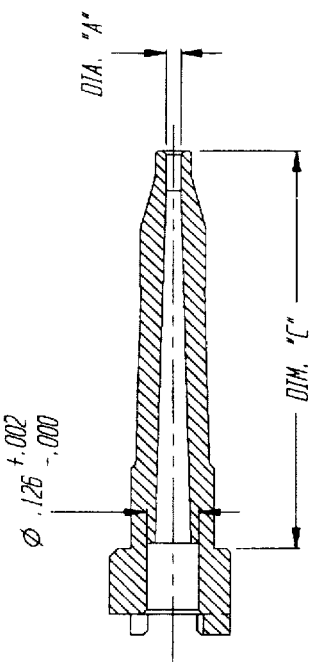

The CDR lock 180 is a spring 210 loaded lever that normal forces an elastomer pad 181 against the CDR 90 which rests against the CDR guide 220. Pressing the lever portion 183 of the lock 180 releases the pad 181 from the CDR 90 allowing it to move longitudinally. The spring 210 is preferably formed of stainless steel and biases the lock 180 against the guide 220 to normally prevent longitudinal movement of the CDR 90. The CDR guide 220 maintains the proper position of the CDR 90 adjacent the lock 180 and allows the CDR 90 to be easily inserted into manifold assembly 150. The guide 220 is preferably formed of injection molded clear polycarbonate, the lock lever 180 is preferably formed of injection molded red polycarbonate and the elastomer pad 181 is preferably formed of polyether-block-amide (e.g. PEBAX). A more detailed view of the lock 180 is illustrated in FIGS. 18a–18g, a more detailed view of the guide is illustrated in FIGS. 22a–22e, and a more detailed view of the spring 210 is illustrated in FIGS. 21a–21c.

The membrane switch panel 270 seals the exterior of the electronic circuit 280 and pressure sensor 282 and provides a method of turning the LCD display 281 on and off. The panel 270 is adhesively bonded to the case top 160 utilizing a pressure sensitive adhesive. The panel 270 has two small tactile dome switches 274 and 275 and a clear viewing area 276 for the LCD display 281. Contact pads 217, 272, 273 facilitate connection of the switch panel 270 to the electronic circuitry 280. Preferably the membrane switch panel 270 is made of polyester. A more detailed view of the membrane switch panel is illustrated in FIGS. 27a and 27b.

Figure 28:
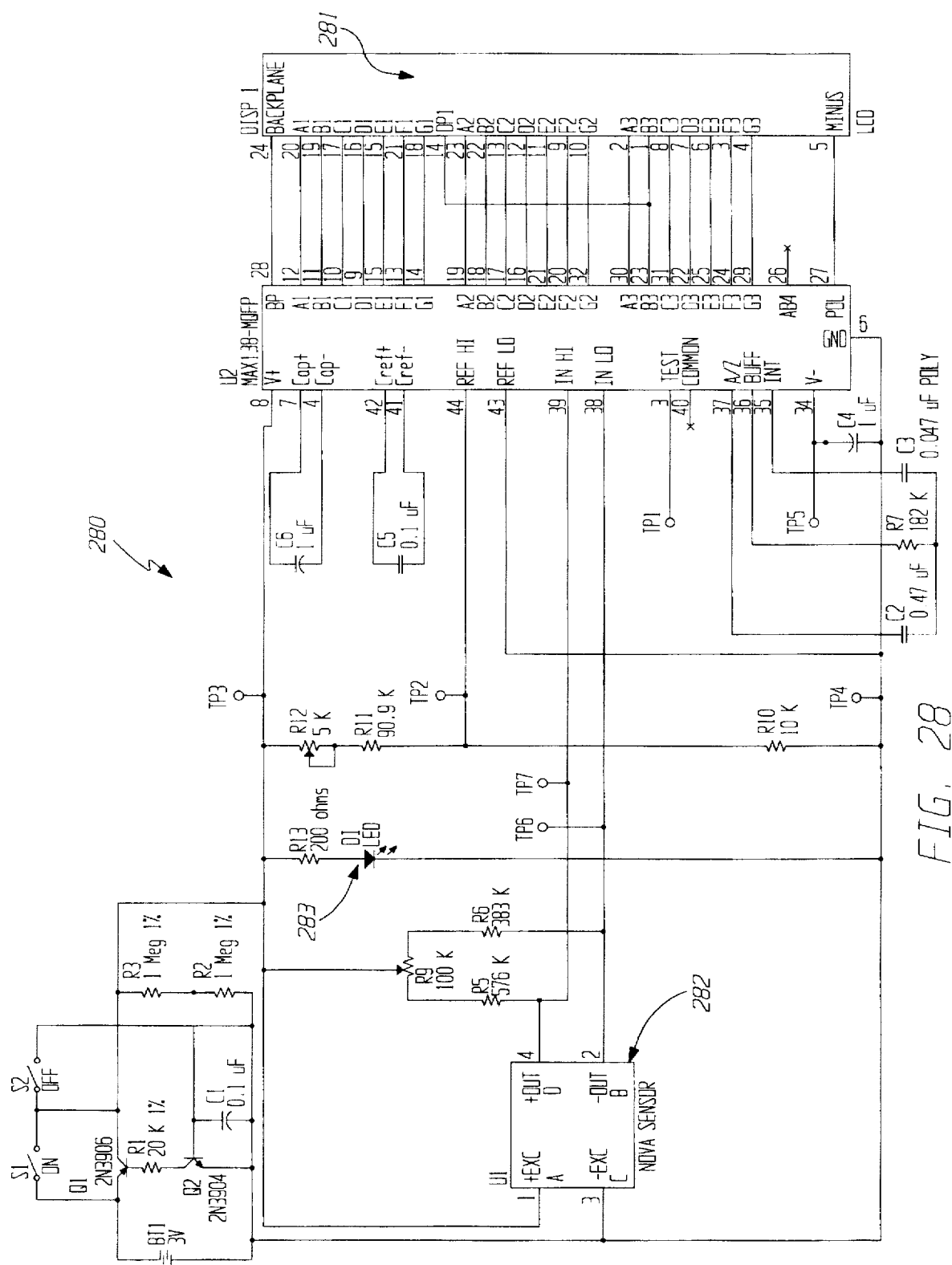
FIG. 28 illustrates a schematic diagram of the electronics incorporated in the manifold assembly shown in FIG. 15.

The electronic circuitry 280 preferably utilizes a piezo electric type pressure sensor 282 (e.g., Lucas Nova Sensor NPC 102) to monitor the pressure inside the sealed chamber 124 and the balloon 84. The electronics 280 are assembled into the case top 160 and interface with the membrane switch panel 270 by way of a flexible conductor tape 159. The pressure of the sealed chamber 124 and the interior of the balloon 84 is displayed on the LCD 281 preferably in units of atmospheres. For viewing in reduced light, the entire display is back-lit utilizing red LED 283 diffused by a clear acrylic plate 158 positioned between the electronic circuitry 280 and the LCD 281. Preferably, the electronic circuitry 280 is encased in a two part epoxy potting material to prevent fluid contact with the unit. A detailed view of the electronic circuitry is illustrated in FIG. 28.

Catheter 80 may be prepped substantially as described with reference to FIGS. 5a–5c. To further facilitate prepping, prepping tools 190 and 200 as shown in FIGS. 19a–19c and 20a–20c may be utilized.

Figure 19D:
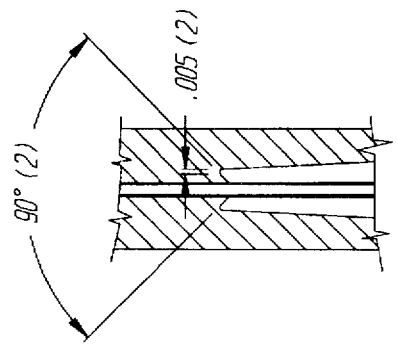
Figure 19C:
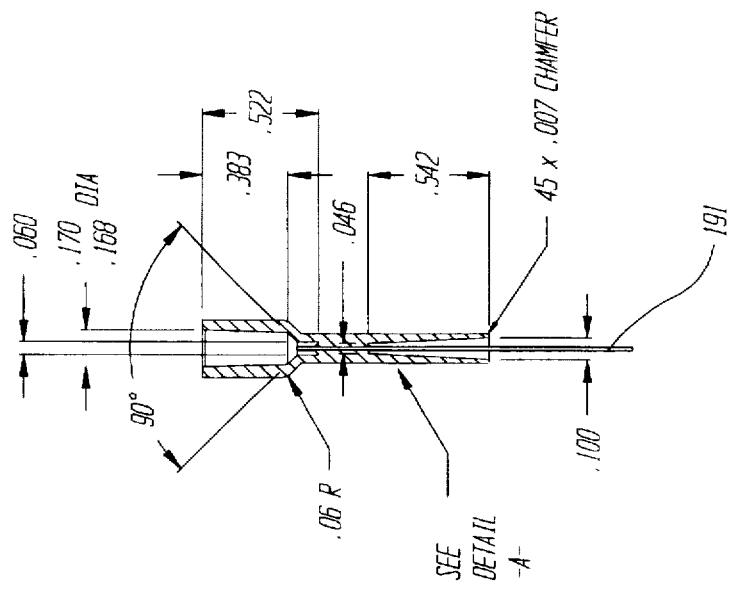
Figure 19B:
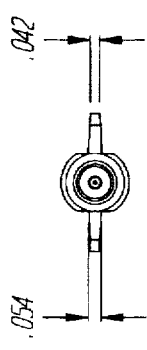
Figure 19A:
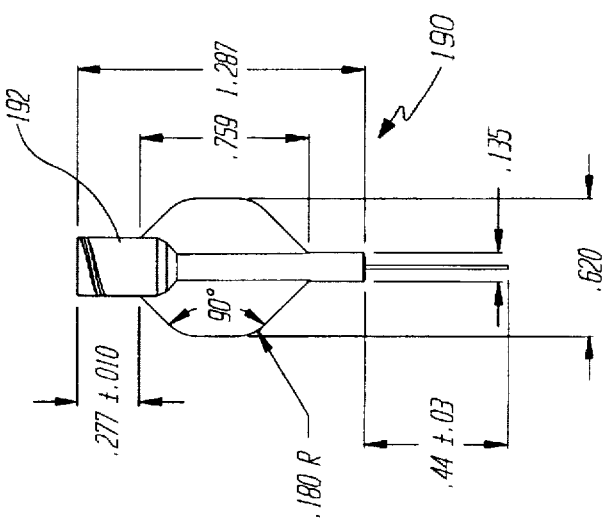

In particular, a prep luer 190 illustrated in FIGS. 19a–19c may be inserted in to the distal end of the guide wire lumen 131 in the distal inner shaft 83. The hypotube 191 on the luer 190 forms a friction seal with the inside surface of the inner shaft 83 and the body portion 192 of the luer facilitates connection to a syringe. As such, a solution of saline and radiopaque contrast media may be injected into the guide wire lumen 131. The body 192 of the prep luer 190 is preferably formed of injection molded red polycarbonate and the hypotube 191, which may be inserted molded into the body 192, is preferably formed of stainless steel having an outside diameter of about 0.016 inches and an inside diameter of about 0.009 inches.

In order to cause the prepping solution to pass through the valve 100 and into the sealed chamber 124, a prep mandrel 200 is inserted into the proximal guide wire port at the proximal end of the inner shaft 83. The prep mandrel 200, which is shown in FIGS. 20a–20c, includes a handle portion 201 and a mandrel portion 202. The mandrel portion 202 is sized and tapered to form a friction fit inside the proximal end of the inner shaft 83 when inserted therein. The handle portion 201 may be formed of injection molded polycarbonate and the mandrel portion 202, which may be inserted molded into the handle 201, is preferably formed of stainless steel having an outside diameter of about 0.016 inches tapering to about 0.010 inches.

With the prep mandrel 200 inserted into the proximal guide wire port, contrast liquid injected via the prep luer 190 is forced across the valve 100 and into the catheter 80. At this point, the CDR 90 is preferably substantially or fully retracted. Note that there is a diminimus amount of air (if any) in the balloon during the prepping procedure because the balloon is preferably folded in to a collapsed state and maintained in that position with one or more snugly fitting balloon protectors. As the contrast solution passes across the valve 100, air is displaced in the proximal direction towards the manifold assembly 150. With the valve stem 230 in the open position, contrast solution flows and displaces air through the sealed chamber 124 and exits out the prep port 244 in the manifold body 240. Once contrast liquid is seen exiting the prep port 244, the valve stem 230 may be rotated into the closed position such that the chamber 124 is completely closed and sealed from the exterior.

With the valve stem 230 closed, the catheter 80 is prepped and ready for use in-vivo. Catheter 80 may be used substantially as described with reference to catheters 10 and 40b.

While the specification describes the preferred materials, dimensions, constructions, manufacturing processes and methods of use, those skilled in the art will appreciate the scope and spirit of the invention with reference to the appended claims. Claims directed to methods or processes may be read without regard as to the order of the steps unless contraindicated by the teachings herein.

What is claimed is:

1. A balloon catheter, comprising:
   a. an elongate tubular member having a proximal end and a distal end;
   b. a balloon connected to the distal end of the elongate tubular member, the balloon having an interior in fluid communication with the inside of the elongate tubular member;
   c. a contrast displacement rod having a portion thereof slidably disposed in the tubular member such that the balloon may be expanded upon longitudinal actuation of the rod, the rod including a stop mechanism to inhibit removal of the rod from the tubular member; and
   d. a seal connected to the proximal end of the tubular member and disposed about the displacement rod to create a liquid seal between the inside of the tubular member and the displacement rod.

2. A balloon catheter as in claim 1, further comprising:
   e. a pressure gauge connected to the proximal end of the elongate tubular member and in fluid communication with the interior of the balloon.

3. A balloon catheter as in claim 2, wherein the seal is an o-ring type seal.

4. A balloon catheter as in claim 2, wherein the seal is a gap tolerance type seal.

5. A balloon catheter as in claim 2, wherein the elongate tubular member contains a guide wire lumen extending at least partially therethrough.

6. A balloon catheter as in claim 5, wherein the guide wire lumen extends the full length of the elongate tubular member.

7. A balloon catheter as in claim 5, wherein the guide wire lumen extends from a point distal of the proximal end of the elongate tubular member to the distal end of the elongate tubular member.

8. A balloon catheter as in claim 5, further comprising;

f. a one-way-valve connected to the distal end of the elongate tubular member, the one-way-valve permitting a pressurized contrast to flow from the guide wire lumen to the interior of the balloon while preventing the pressurized contrast to flow from the interior of the balloon to the guide wire lumen.

9. A balloon catheter as in claim 8, wherein the proximal end of the guide wire lumen is releasably connected to a contrast plug and the distal end of the guide wire lumen is releasably connected to a pressurized contrast source.

10. A balloon catheter as in claim 9, wherein the pressurized liquid source is releasably connected to the distal end of the guide wire lumen with a tubular member disposed about the balloon.

11. A balloon catheter as in claim 10, wherein the tubular member retains the balloon in a contracted state.

12. A balloon catheter as in claim 11, wherein a portion of the elongate tubular member traverses the interior of the balloon.

13. A balloon catheter as in claim 12, wherein the one-way-valve is connected to the portion of the elongate tubular member which traverses the interior of the balloon.

14. A balloon catheter as in claim 13, wherein the one-way-valve includes an elastomer tube disposed about a hole in the portion of the elongate tubular member which traverses the interior of the balloon.

15. A balloon catheter as in claim 2, wherein the elongate tubular member contains a core wire fixed therein, the core wire having a distally mounted spring tip.

16. A method of using a balloon catheter, comprising the steps of:

a. providing a balloon catheter wherein the balloon catheter includes:
   i. an elongate tubular member having a proximal end and a distal end;
   ii. a balloon connected to the distal end of the elongate tubular member, the balloon having an interior in fluid communication with the inside of the elongate tubular member;
   iii. a contrast displacement rod having a portion thereof slidably disposed in the tubular member such that the balloon may be expanded upon longitudinal actuation of the rod, the rod including a stop mechanism to inhibit removal of the rod from the tubular member; and
   iv. a seal connected to the proximal end of the tubular member and disposed about the displacement rod to create a liquid seal between the inside of the tubular member and the displacement rod;

b. inserting the balloon catheter into a vascular system of a patient;

c. positioning the balloon catheter adjacent a treatment site in the vascular system;

d. displacing the rod to at least partially expand the balloon;

e. displacing the rod to at least partially contract the balloon; and f. withdrawing the balloon catheter from the vascular system.

* * * * *

UNITED STATES PATENT AND TRADEMARK OFFICE
CERTIFICATE OF CORRECTION

PATENT NO. : 5,785,685

DATED : July 28, 1998

INVENTOR(S) : KUGLER et al.

It is certified that error appears in the above-identified patent and that said Letters Patent is hereby corrected as shown below:

Title page, item [56] References Cited, U.S. Patent Documents, insert:

| | | |
|---|---|---|
| --3,726,283 | 4/1973 | Dye et al. |
| 5,180,364 | 1/1993 | Ginsburg |
| 5,035,705 | 7/1991 | Burns |
| 5,378,238 | 1/1995 | Peters et al. |
| 5,217,434 | 6/1993 | Arney |
| 5,100,385 | 3/1992 | Bromander |
| 4,930,341 | 6/1990 | Euteneuer |
| 5,049,130 | 9/1991 | Powell |
| 5,273,529 | 12/1993 | Idowu |
| 4,593,690 | 6/1986 | Sheridan et al. |
| 5,334,153 | 8/1994 | McIntyre et al. |
| 5,338,301 | 8/1994 | Diaz |
| 4,479,497 | 10/1984 | Fogarty et al. |
| 4,564,014 | 1/1986 | Fogarty et al. |
| 4,652,259 | 3/1987 | O'Neil |
| 4,762,130 | 8/1988 | Fogarty et al. |
| 5,152,277 | 10/1992 | Honda et al. |
| 5,180,367 | 1/1993 | Kontos et al. |

UNITED STATES PATENT AND TRADEMARK OFFICE
CERTIFICATE OF CORRECTION

PATENT NO. : 5,785,685

DATED : July 28, 1998

INVENTOR(S) : KUGLER et al.

It is certified that error appears in the above-identified patent and that said Letters Patent is hereby corrected as shown below:

| | | |
|---|---|---|
| 5,242,398 | 9/1993 | Knoll |
| 5,246,420 | 9/1993 | Kraus et al. |
| 5,306,261 | 4/1994 | Alliger et al. |
| 5,275,169 | 1/1994 | Afromowitz et al. |
| 5,265,593 | 11/1993 | Odland |
| 5,318,533 | 6/1994 | Adams et al. |
| 3,190,291 | 6/1965 | Foley |
| 3,378,011 | 4/1968 | Vitello |
| 3,379,197 | 4/1968 | Hayes |
| 3,602,226 | 8/1971 | Ericson |
| 3,675,658 | 7/1972 | Taylor |
| 3,818,903 | 6/1974 | Bleecker |
| 4,227,534 | 10/1980 | LaRosa |
| 4,244,366 | 1/1981 | Raines |
| 4,446,867 | 5/1984 | Leveen et al. |
| 4,476,866 | 10/1984 | Chin |
| 4,535,757 | 8/1985 | Webster, Jr. |
| 4,592,364 | 6/1986 | Pinto |
| 4,651,738 | 3/1987 | Demer et al. |

UNITED STATES PATENT AND TRADEMARK OFFICE
CERTIFICATE OF CORRECTION

PATENT NO. : 5,785,685

DATED : July 28, 1998

INVENTOR(S) : KUGLER et al.

It is certified that error appears in the above-identified patent and that said Letters Patent is hereby corrected as shown below:

| | | |
|---|---|---|
| 4,655,749 | 4/1987 | Fischione |
| 4,740,203 | 4/1988 | Hoskins et al. |
| 4,758,223 | 7/1988 | Rydell |
| 4,781,192 | 11/1988 | Demer |
| 4,838,864 | 6/1989 | Peterson |
| 4,878,903 | 11/1989 | Mueller |
| 4,929,238 | 5/1990 | Baum |
| 4,944,726 | 7/1990 | Hilal et al. |
| 4,954,239 | 9/1990 | Mueller |
| 5,004,472 | 4/1991 | Wallace |
| 5,009,662 | 4/1991 | Wallace et al. |
| 5,019,041 | 5/1991 | Robinson et al. |
| 5,021,046 | 6/1991 | Wallace |
| 5,113,868 | 5/1992 | Wise et al. |
| 5,152,776 | 10/1992 | Pinchuk |
| 5,156,598 | 10/1992 | Skakoon et al. |
| 5,171,299 | 12/1992 | Heitzmann et al. |
| 5,196,017 | 3/1993 | Silva et al. |

UNITED STATES PATENT AND TRADEMARK OFFICE
CERTIFICATE OF CORRECTION

PATENT NO. : 5,785,685　　　　　　　　　　　PAGE  4  of  6

DATED     : July 28, 1998

INVENTOR(S): KUGLER et al.

It is certified that error appears in the above-identified patent and that said Letters Patent is hereby corrected as shown below:

| | | |
|---|---|---|
| 5,209,728 | 5/1993 | Kraus et al. |
| 5,215,523 | 6/1993 | Williams et al. |
| 5,273,537 | 12/1993 | Haskvitz et al. |
| 5,284,480 | 2/1994 | Porter et al. |
| 4,332,254 | 6/1982 | Lundquist |
| 4,723,938 | 2/1988 | Goodin et al. |
| 4,919,121 | 4/1990 | Rydell et al. |
| 5,342,298 | 8/1994 | Michaels et al. |
| 4,245,639 | 1/1981 | La Rosa |
| 4,370,982 | 2/1983 | Reilly |
| 4,413,989 | 11/1983 | Schjeldahl et al. |
| 4,429,724 | 2/1984 | Dorros et al. |
| 4,439,185 | 3/1984 | Lundquist-- |

Title page, in [56] References Cited, Foreign Patent Documents, insert:

| | | |
|---|---|---|
| --WO92/03095 | 3/1992 | WIPO |
| WO93/17750 | 9/1993 | WIPO |
| GB2209121 | 5/1989 | United Kingdom-- |

UNITED STATES PATENT AND TRADEMARK OFFICE
CERTIFICATE OF CORRECTION

PATENT NO. : 5,785,685

DATED : July 28, 1998

INVENTOR(S) : KUGLER et al.

It is certified that error appears in the above-identified patent and that said Letters Patent is hereby corrected as shown below:

Title page, in [56] References Cited, Other Publications, insert:

--R. Cooper et al.; "Angioplasty for coarctation of the aorta: long-term results", *American Heart Association Circulation* brochure, *THERAPY AND PREVENTION CONGENITAL HEART DISEASE*, Vol. 75, No. 3, Mar. 1987, pp. 600-604.

Grollier et al., "Anterograde percutaneous transseptal valvuloplasty in a case of severe calcific aortic stenosis", *European Heart Journal*, Vol. 8, Feb. 1987, pp. 190-192.

P.S. Rao, "Balloon Aortic Valvuloplasty in Children", *Clinical Cardiology*, Vol. 13, Jul. 1990, pp. 458-466.

J. Abele, "Balloon Catheters and Transluminal Dilatation: Technical Considerations", *American Journal of Roentgenology*, Vol. 135, Nov. 1980, pp. 901-906.

Hjemdahl-Monsen et al., "Angiographic Patterns of Balloon Inflation During Percutaneous Transluminal Coronary Angioplasty: Role of Pressure-Diameter Curves in Studying Distensibility and Elasticity of the Stenotic Lesion and the Mechanism of Dilation", *Journal of the American College of Cardiology*, Vol. 16, No. 3, Sept. 1990, pp. 569-575.

Demer et al., "High Intensity Ultrasound Increases Distensibility of Calcific Atherosclerotic Arteries", *Journal of the American College of Cardiology*, Vol. 18, No. 5, Nov. 1991, pp. 1259-62.--

UNITED STATES PATENT AND TRADEMARK OFFICE
CERTIFICATE OF CORRECTION

PATENT NO. : 5,785,685

DATED : July 28, 1998

INVENTOR(S) : KUGLER et al.

It is certified that error appears in the above-identified patent and that said Letters Patent is hereby corrected as shown below:

At column 16, line 22, "12.50°" should be --12.5°--.

At column 17, line 28, "a traumatic" should be --atraumatic--.

Signed and Sealed this

Sixteenth Day of March, 1999

Attest:

Q. TODD DICKINSON

Attesting Officer

Acting Commissioner of Patents and Trademarks